US012562256B2

(12) United States Patent
    Yarmarkovich et al.

(10) Patent No.: US 12,562,256 B2
(45) Date of Patent: Feb. 24, 2026

(54) SYSTEMS, METHODS AND COMPUTER-ACCESSIBLE MEDIUM FOR IDENTIFYING TARGET PAIRS FOR CAR-T THERAPY

(71) Applicant: NEW YORK UNIVERSITY, New York, NY (US)

(72) Inventors: Mark Yarmarkovich, New York, NY (US); Zachary Harpaz, Boca Raton, FL (US); Guangyuan Li, New York, NY (US); Michele Palamenghi, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 18/940,364

(22) Filed: Nov. 7, 2024

(65) Prior Publication Data

US 2025/0218563 A1     Jul. 3, 2025

Related U.S. Application Data

(60) Provisional application No. 63/547,619, filed on Nov. 7, 2023.

(51) Int. Cl.
    *G16H 20/40*        (2018.01)
    *G16H 50/20*        (2018.01)
(52) U.S. Cl.
    CPC ............. *G16H 20/40* (2018.01); *G16H 50/20* (2018.01)
(58) Field of Classification Search
    CPC ............................... G16H 20/40; G16H 50/20
    See application file for complete search history.

(56) References Cited

U.S. PATENT DOCUMENTS

| | | | | | |
|---|---|---|---|---|---|
| 6,410,014 B1 * | 6/2002 | Seed | ...................... | A61K 35/13 | 435/372.3 |
| 6,428,953 B1 * | 8/2002 | Naldini | ................... | C12N 7/00 | 435/456 |
| 6,475,769 B1 * | 11/2002 | Wilson | ................... | C12N 15/86 | 435/235.1 |
| 6,489,458 B2 * | 12/2002 | Hackett | ................. | C12N 15/90 | 435/445 |
| 6,534,055 B1 * | 3/2003 | June | ................. | C07K 14/70521 | 435/375 |

(Continued)

OTHER PUBLICATIONS

Andrés-Galiana, Elsevier, 2019, pp. 1-8.*

(Continued)

*Primary Examiner* — Michael I Ezewoko
(74) *Attorney, Agent, or Firm* — HUNTON ANDREWS KURTH LLP

(57)        ABSTRACT

Exemplary systems, methods, and computer-accessible medium are provided for Chimeric Antigen Receptor (CAR)-T therapy. Thus, the exemplary systems, methods, and computer-accessible medium are provided that select a first set of targets highly expressed in cancer and lowly in normal tissues, select a second set of targets that are highly co-expressed in the cancer and lowly in normal tissues, generate an input set by combining the first and second set of targets with dependency data, single-cell heterogeneity, and antibody availability, determine, by a learning model, at least one target pair for use in CAR-T therapy, and apply a cell therapy based on the determined target pair(s).

24 Claims, 19 Drawing Sheets

(56)             References Cited

U.S. PATENT DOCUMENTS

| | | | | |
|---|---|---|---|---|
| 6,537,540 B1* | 3/2003 | Burstein | A61P 19/02 | 435/456 |
| 6,537,594 B1* | 3/2003 | Paoletti | C07K 14/33 | 435/69.51 |
| 6,569,457 B2* | 5/2003 | Ullah | A61K 31/7048 | 424/475 |
| 6,638,534 B1* | 10/2003 | Ishibashi | A61K 9/5078 | 424/494 |
| 6,682,743 B2* | 1/2004 | Mayr | A61K 39/285 | 435/235.1 |
| 6,713,068 B1* | 3/2004 | Audonnet | A61K 39/39 | 435/5 |
| 6,753,162 B1* | 6/2004 | Seed | A61K 40/31 | 435/69.1 |
| 6,761,893 B2* | 7/2004 | Chaplin | A61P 31/20 | 435/235.1 |
| 6,780,407 B1* | 8/2004 | Paoletti | C07K 14/5434 | 435/320.1 |
| 6,780,417 B2* | 8/2004 | Kaslow | C07K 14/445 | 435/69.3 |
| 6,793,926 B1* | 9/2004 | Rasty | C12N 15/86 | 435/235.1 |
| 6,797,514 B2* | 9/2004 | Berenson | C07K 16/2803 | 436/526 |
| 6,821,515 B1* | 11/2004 | Cleland | A61P 35/00 | 424/138.1 |
| 6,867,041 B2* | 3/2005 | Berenson | C07K 16/2833 | 436/526 |
| 6,869,794 B2* | 3/2005 | Vogels | C12N 7/025 | 435/235.1 |
| 6,887,466 B2* | 5/2005 | June | C07K 16/2833 | 435/375 |
| 6,893,865 B1* | 5/2005 | Lockert | C12N 7/00 | 424/94.4 |
| 6,905,680 B2* | 6/2005 | June | C07K 16/2812 | 435/375 |
| 6,905,681 B1* | 6/2005 | June | C07K 16/289 | 435/375 |
| 6,905,874 B2* | 6/2005 | Berenson | C07K 16/2875 | 436/526 |
| 6,913,752 B2* | 7/2005 | Chaplin | A61K 39/12 | 435/235.1 |
| 6,913,922 B1* | 7/2005 | Bout | C12N 15/86 | 435/456 |
| 6,923,973 B1* | 8/2005 | Cox | A61K 39/0002 | 424/274.1 |
| 6,924,128 B2* | 8/2005 | Allen | C12N 7/00 | 435/456 |
| 6,936,466 B2* | 8/2005 | Feldhaus | C12N 15/86 | 435/235.1 |
| 6,943,019 B2* | 9/2005 | Wilson | C12N 15/86 | 435/235.1 |
| 6,953,690 B1* | 10/2005 | Gao | A61K 48/0091 | 435/456 |
| 6,955,808 B2* | 10/2005 | Curiel | C12N 15/86 | 435/456 |
| 6,974,695 B2* | 12/2005 | Vogels | C12N 15/861 | 435/235.1 |
| 6,991,797 B2* | 1/2006 | Andersen | A61K 39/04 | 424/234.1 |
| 7,029,848 B2* | 4/2006 | Vogels | C12N 15/86 | 435/235.1 |
| 7,045,313 B1* | 5/2006 | Moss | A61K 39/275 | 435/235.1 |
| 7,097,842 B2* | 8/2006 | Suter | C12N 15/86 | 435/235.1 |
| 7,115,391 B1* | 10/2006 | Chen | C12N 15/86 | 435/456 |
| 7,144,575 B2* | 12/2006 | June | C07K 14/70532 | 435/375 |
| 7,148,203 B2* | 12/2006 | Hackett | C12N 15/90 | 536/23.4 |
| 7,160,682 B2* | 1/2007 | Hackett | C12N 9/22 | 536/23.4 |
| 7,172,893 B2* | 2/2007 | Rabinowitz | A61P 21/04 | 435/235.1 |
| 7,175,843 B2* | 2/2007 | June | C07K 16/2896 | 435/375 |
| 7,189,536 B2* | 3/2007 | Chaplin | A61P 31/14 | 435/235.1 |
| 7,198,784 B2* | 4/2007 | Kingsman | A61K 48/0091 | 435/325 |
| 7,232,566 B2* | 6/2007 | June | C07K 16/289 | 435/375 |
| 7,255,862 B1* | 8/2007 | Tartaglia | C07K 14/005 | 424/188.1 |
| 7,259,015 B2* | 8/2007 | Kingsman | A61P 25/16 | 435/456 |
| 7,283,337 B2* | 10/2007 | Sakai | G11B 5/3932 | 360/324.12 |
| 7,303,910 B2* | 12/2007 | Bebbington | C07K 14/005 | 435/320.1 |
| 7,335,364 B2* | 2/2008 | Chaplin | C07K 14/005 | 435/235.1 |
| 7,351,585 B2* | 4/2008 | Mitrophanous | C12N 15/86 | 435/325 |
| 7,384,644 B2* | 6/2008 | Chaplin | A61P 31/12 | 435/237 |
| 7,445,924 B2* | 11/2008 | Chaplin | A61K 39/12 | 435/239 |
| 7,459,270 B2* | 12/2008 | Chaplin | A61P 43/00 | 435/235.1 |
| 7,529,685 B2* | 5/2009 | Davies | G16Z 99/00 | 707/999.005 |
| 7,572,631 B2* | 8/2009 | Berenson | A61K 40/42 | 435/375 |
| 7,608,279 B2* | 10/2009 | Parisot | A61P 31/10 | 424/283.1 |
| 7,628,980 B2* | 12/2009 | Suter | A61K 38/212 | 435/235.1 |
| 7,705,120 B2* | 4/2010 | Lillie | C12Q 1/6886 | 536/23.4 |
| 7,708,949 B2* | 5/2010 | Stone | B01F 25/45 | 422/68.1 |
| 7,741,465 B1* | 6/2010 | Eshhar | C07K 16/32 | 435/325 |
| 7,767,449 B1* | 8/2010 | Paoletti | C07K 14/005 | 435/235.1 |
| 7,892,533 B2* | 2/2011 | Suter | A61K 38/215 | 435/235.1 |
| 7,897,156 B2* | 3/2011 | Ackermann | A61P 37/04 | 424/281.1 |
| 7,923,017 B2* | 4/2011 | Chaplin | C12N 7/00 | 435/235.1 |
| 7,939,086 B2* | 5/2011 | Chaplin | A61P 35/00 | 435/235.1 |
| 7,964,395 B2* | 6/2011 | Chaplin | A61K 39/12 | 435/235.1 |
| 7,964,396 B2* | 6/2011 | Chaplin | C12N 15/86 | 435/235.1 |
| 7,964,398 B2* | 6/2011 | Chaplin | A61K 39/12 | 435/235.1 |
| 7,985,739 B2* | 7/2011 | Kay | C12N 9/22 | 435/320.1 |
| 8,034,334 B2* | 10/2011 | Dudley | A61K 39/0011 | 435/372.3 |
| 8,088,379 B2* | 1/2012 | Robbins | G01N 33/505 | 435/7.1 |
| 8,163,293 B2* | 4/2012 | Chaplin | A61P 35/00 | 424/199.1 |
| 8,211,422 B2* | 7/2012 | Eshhar | A61K 40/4205 | 514/44 R |
| 8,227,432 B2* | 7/2012 | Hackett | C12N 9/22 | 536/23.1 |
| 8,236,560 B2* | 8/2012 | Chaplin | C07K 14/005 | 435/235.1 |
| 8,268,325 B2* | 9/2012 | Chaplin | C07K 14/005 | 424/199.1 |

(56)          References Cited

U.S. PATENT DOCUMENTS

| | | | | |
|---|---|---|---|---|
| 8,268,329 | B2* | 9/2012 | Chaplin | A61P 35/00 |
| | | | | 435/5 |
| 8,278,036 | B2* | 10/2012 | Kariko | C12Y 305/04004 |
| | | | | 435/375 |
| 8,309,098 | B2* | 11/2012 | Howley | A61P 31/18 |
| | | | | 424/199.1 |
| 8,372,622 | B2* | 2/2013 | Suter | A61K 38/212 |
| | | | | 435/235.1 |
| 8,392,127 | B2* | 3/2013 | Watters | C12Q 1/6886 |
| | | | | 435/6.13 |
| 8,399,645 | B2* | 3/2013 | Campana | A61P 35/00 |
| | | | | 536/23.4 |
| 8,404,658 | B2* | 3/2013 | Hajjar | A61P 9/00 |
| | | | | 514/44 A |
| 8,454,972 | B2* | 6/2013 | Nabel | A61P 37/04 |
| | | | | 424/202.1 |
| 8,470,598 | B2* | 6/2013 | Chaplin | A61K 39/12 |
| | | | | 435/235.1 |
| 8,557,779 | B2* | 10/2013 | Sugiyama | A61K 40/4243 |
| | | | | 514/19.3 |
| 8,589,175 | B2* | 11/2013 | Glauser | G16H 50/50 |
| | | | | 600/300 |
| 8,697,854 | B2* | 4/2014 | Schendel | C12N 15/85 |
| | | | | 536/23.5 |
| 8,796,414 | B2* | 8/2014 | Johnston | A61P 35/00 |
| | | | | 530/300 |
| 8,843,356 | B2* | 9/2014 | Schadt | G16B 25/10 |
| | | | | 703/11 |
| 8,906,682 | B2* | 12/2014 | June | C12N 7/00 |
| | | | | 435/372.3 |
| 8,911,993 | B2* | 12/2014 | June | C12N 7/00 |
| | | | | 435/372.3 |
| 8,916,381 | B1* | 12/2014 | June | A61K 40/11 |
| | | | | 435/372.3 |
| 8,975,071 | B1* | 3/2015 | June | C07K 16/2803 |
| | | | | 435/372.3 |
| 9,101,584 | B2* | 8/2015 | June | A61K 48/005 |
| 9,102,760 | B2* | 8/2015 | June | A61P 35/00 |
| 9,102,761 | B2* | 8/2015 | June | A61P 43/00 |
| 9,115,402 | B2* | 8/2015 | Hacohen | A61K 40/42 |
| 9,342,657 | B2* | 5/2016 | Wei | G16H 50/70 |
| 9,556,237 | B2* | 1/2017 | Schmaljohn | C07K 14/175 |
| 9,909,159 | B2* | 3/2018 | Marras | C12Q 1/686 |
| 9,962,453 | B2* | 5/2018 | Georges | A61P 31/00 |
| 10,144,927 | B2* | 12/2018 | Kampmann | C12N 15/111 |
| 10,185,803 | B2* | 1/2019 | Frey | G16B 40/20 |
| 10,202,640 | B2* | 2/2019 | Davis | C12Q 1/686 |
| 10,249,389 | B2* | 4/2019 | Athey | G06N 3/098 |
| 10,360,499 | B2* | 7/2019 | Kumar | G06N 3/0464 |
| 10,395,772 | B1* | 8/2019 | Lucas | G16H 10/60 |
| 10,426,824 | B1* | 10/2019 | Hacohen | G01N 33/574 |
| 10,553,318 | B2* | 2/2020 | Athey | G16H 50/30 |
| 10,665,326 | B2* | 5/2020 | Aliper | G16B 40/30 |
| 10,801,070 | B2* | 10/2020 | Clement | G16B 30/00 |
| 10,975,442 | B2* | 4/2021 | Hacohen | G01N 33/57407 |
| 11,087,460 | B2* | 8/2021 | Buckler | G06T 7/0012 |
| 11,164,082 | B2* | 11/2021 | Kumar | G16B 40/20 |
| 11,321,327 | B2* | 5/2022 | Stennett | G06F 16/24568 |
| 11,400,116 | B2* | 8/2022 | Lim | G16Z 99/00 |
| 11,403,316 | B2* | 8/2022 | Lee | G16B 40/00 |
| 11,410,763 | B2* | 8/2022 | Frieder | G06F 18/24137 |
| 11,424,008 | B2* | 8/2022 | Lee | G06N 3/0985 |
| 11,436,246 | B2* | 9/2022 | Lee | G16H 10/20 |
| 11,452,768 | B2* | 9/2022 | Hacohen | A61K 39/0011 |
| 11,640,859 | B2* | 5/2023 | Colley | G16H 20/00 |
| | | | | 702/19 |
| 11,705,226 | B2* | 7/2023 | Colley | G16B 40/00 |
| | | | | 705/3 |
| 11,725,237 | B2* | 8/2023 | Shukla | G16B 20/00 |
| | | | | 702/19 |
| 11,834,718 | B2* | 12/2023 | Clement | G16B 30/00 |
| 11,869,664 | B2* | 1/2024 | Frieder | G06F 18/24137 |
| 11,887,696 | B2* | 1/2024 | Frey | G16B 30/00 |
| 11,939,637 | B2* | 3/2024 | Hacohen | C12Q 1/6886 |
| 11,967,400 | B2* | 4/2024 | Lee | G16B 10/00 |
| 12,009,061 | B2* | 6/2024 | Peters | G16B 40/20 |
| 12,073,561 | B2* | 8/2024 | Buckler | G06F 18/211 |
| 12,087,404 | B2* | 9/2024 | Lee | G06N 3/0455 |
| 12,112,839 | B2* | 10/2024 | Colley | G16H 20/10 |
| 12,125,572 | B2* | 10/2024 | Buckler | G16B 5/00 |
| 12,131,472 | B2* | 10/2024 | Buckler | G06N 3/0464 |
| 12,141,975 | B2* | 11/2024 | Buckler | G06N 3/096 |
| 12,159,406 | B2* | 12/2024 | Buckler | G06N 3/096 |
| 12,211,623 | B2* | 1/2025 | Frieder | G06N 5/022 |
| 12,229,957 | B2* | 2/2025 | Buckler | G06T 3/00 |
| 12,236,595 | B2* | 2/2025 | Buckler | G06V 10/82 |
| 12,260,939 | B2* | 3/2025 | Garcia | G16B 25/10 |
| 12,336,804 | B2* | 6/2025 | Narayan | A61B 5/7267 |
| 12,383,196 | B2* | 8/2025 | Etkin | A61B 5/377 |
| 12,394,524 | B2* | 8/2025 | Ng | G06N 3/08 |
| 2003/0046114 | A1* | 3/2003 | Davies | G16Z 99/00 |
| | | | | 705/3 |
| 2003/0104008 | A1* | 6/2003 | Loosmore | C07K 14/005 |
| | | | | 424/199.1 |
| 2004/0013648 | A1* | 1/2004 | Kingsman | A61P 25/28 |
| | | | | 435/235.1 |
| 2004/0053304 | A1* | 3/2004 | Markowitz | A61P 35/00 |
| | | | | 435/325 |
| 2006/0008468 | A1* | 1/2006 | Chiang | A61K 39/001184 |
| | | | | 424/193.1 |
| 2006/0163385 | A1* | 7/2006 | Link | B01F 25/45 |
| | | | | 239/423 |
| 2006/0252077 | A1* | 11/2006 | Buzby | C12Q 1/6869 |
| | | | | 435/6.12 |
| 2006/0258607 | A1* | 11/2006 | Jarosch | A61P 3/04 |
| | | | | 435/6.16 |
| 2007/0003442 | A1* | 1/2007 | Link | B01F 25/45211 |
| | | | | 422/400 |
| 2007/0025970 | A1* | 2/2007 | Kingsman | A61P 25/16 |
| | | | | 435/456 |
| 2007/0055049 | A1* | 3/2007 | Grey | C07K 14/70539 |
| | | | | 530/350 |
| 2007/0083334 | A1* | 4/2007 | Mintz | G16B 40/00 |
| | | | | 702/19 |
| 2007/0134197 | A1* | 6/2007 | Eichner | A61P 37/04 |
| | | | | 424/85.7 |
| 2007/0143149 | A1* | 6/2007 | Buttner | G16H 10/60 |
| | | | | 705/3 |
| 2007/0184489 | A1* | 8/2007 | Griffiths | B01L 3/502761 |
| | | | | 435/7.1 |
| 2007/0195127 | A1* | 8/2007 | Ahn | G01N 15/1404 |
| | | | | 347/55 |
| 2008/0003142 | A1* | 1/2008 | Link | B01L 3/565 |
| | | | | 264/219 |
| 2008/0014222 | A1* | 1/2008 | Simmons | A61K 40/11 |
| | | | | 424/277.1 |
| 2008/0254008 | A1* | 10/2008 | Dropulic | A61K 39/12 |
| | | | | 435/5 |
| 2009/0005254 | A1* | 1/2009 | Griffiths | B01J 19/0046 |
| | | | | 506/7 |
| 2009/0026082 | A1* | 1/2009 | Rothberg | G01N 27/414 |
| | | | | 422/400 |
| 2009/0055944 | A1* | 2/2009 | Korman | A61P 1/16 |
| | | | | 424/1.49 |
| 2009/0111106 | A1* | 4/2009 | Mitrophanous | A61P 25/16 |
| | | | | 435/235.1 |
| 2009/0131543 | A1* | 5/2009 | Weitz | B82Y 30/00 |
| | | | | 366/177.1 |
| 2009/0136494 | A1* | 5/2009 | Ponath | A61P 1/04 |
| | | | | 424/133.1 |
| 2009/0186042 | A1* | 7/2009 | Johnston | A61P 35/00 |
| | | | | 530/387.9 |
| 2009/0220980 | A1* | 9/2009 | Hoon | C12Q 1/6886 |
| | | | | 435/6.12 |
| 2010/0137143 | A1* | 6/2010 | Rothberg | G01N 27/4145 |
| | | | | 506/38 |
| 2010/0137163 | A1* | 6/2010 | Link | C12Q 1/6876 |
| | | | | 506/40 |

(56) References Cited

U.S. PATENT DOCUMENTS

| | | | | | |
|---|---|---|---|---|---|
| 2010/0158951 | A1* | 6/2010 | Randolph | | A61P 37/04 |
| | | | | | 424/278.1 |
| 2010/0203531 | A1* | 8/2010 | Sarkaria | | C12Q 1/6886 |
| | | | | | 435/6.12 |
| 2010/0210529 | A1* | 8/2010 | van der Burg | | A61P 35/00 |
| | | | | | 514/19.3 |
| 2010/0282617 | A1* | 11/2010 | Rothberg | | H10D 30/68 |
| | | | | | 205/780.5 |
| 2010/0297071 | A1* | 11/2010 | Ishibashi | | A61P 35/00 |
| | | | | | 424/85.5 |
| 2010/0304989 | A1* | 12/2010 | Von Hoff | | G16H 50/20 |
| | | | | | 506/9 |
| 2011/0015869 | A1* | 1/2011 | Watters | | G16B 40/20 |
| | | | | | 702/19 |
| 2011/0097312 | A1* | 4/2011 | Molldrem | | A61K 40/4247 |
| | | | | | 424/277.1 |
| 2011/0257890 | A1* | 10/2011 | Weinschenk | | G01N 33/6878 |
| | | | | | 702/19 |
| 2011/0293571 | A1* | 12/2011 | Widdowson | | A61P 25/08 |
| | | | | | 435/320.1 |
| 2011/0293637 | A1* | 12/2011 | Hacohen | | G01N 33/57492 |
| | | | | | 424/277.1 |
| 2012/0004893 | A1* | 1/2012 | Vaidyanathan | | G16H 50/50 |
| | | | | | 703/11 |
| 2012/0082691 | A1* | 4/2012 | Rammensee | | A61K 39/001193 |
| | | | | | 424/185.1 |
| 2012/0219947 | A1* | 8/2012 | Yurkovetsky | | B01F 25/14 |
| | | | | | 435/6.11 |
| 2012/0244133 | A1* | 9/2012 | Rosenberg | | A61P 35/00 |
| | | | | | 435/372 |
| 2012/0288539 | A1* | 11/2012 | Eber | | A61K 9/10 |
| | | | | | 514/21.1 |
| 2012/0295960 | A1* | 11/2012 | Palfi | | C12N 15/86 |
| | | | | | 514/44 R |
| 2013/0071414 | A1* | 3/2013 | Dotti | | C12N 15/86 |
| | | | | | 435/320.1 |
| 2013/0210014 | A1* | 8/2013 | Sharman | | C12Q 1/6886 |
| | | | | | 435/6.12 |
| 2013/0295110 | A1* | 11/2013 | Binder | | A61K 39/001194 |
| | | | | | 424/277.1 |
| 2014/0056986 | A1* | 2/2014 | Desai | | A61P 35/00 |
| | | | | | 424/491 |
| 2014/0178438 | A1* | 6/2014 | Sahin | | G16B 20/20 |
| | | | | | 424/277.1 |
| 2014/0256595 | A1* | 9/2014 | Link | | C40B 60/08 |
| | | | | | 506/16 |
| 2014/0322716 | A1* | 10/2014 | Robins | | C12Q 1/6881 |
| | | | | | 435/6.12 |
| 2014/0365242 | A1* | 12/2014 | Neff | | G16H 10/60 |
| | | | | | 707/756 |
| 2015/0072893 | A1* | 3/2015 | Kampmann | | C12N 15/1075 |
| | | | | | 506/10 |
| 2015/0140041 | A1* | 5/2015 | Vitiello | | C12Q 1/6874 |
| | | | | | 424/277.1 |
| 2015/0224182 | A1* | 8/2015 | Hunt | | A61K 39/001156 |
| | | | | | 435/325 |
| 2015/0324527 | A1* | 11/2015 | Siegel | | G16B 50/30 |
| | | | | | 705/3 |
| 2016/0008447 | A1* | 1/2016 | Hacohen | | A61P 35/00 |
| | | | | | 424/174.1 |
| 2016/0101170 | A1* | 4/2016 | Hacohen | | A61K 39/0011 |
| | | | | | 424/277.1 |
| 2016/0213771 | A1* | 7/2016 | Sampson | | A61K 38/164 |
| 2016/0306917 | A1* | 10/2016 | Wei | | A61K 31/555 |
| 2016/0310584 | A1* | 10/2016 | Fritsch | | A61K 47/26 |
| 2016/0326593 | A1* | 11/2016 | Clement | | G16B 30/10 |
| 2016/0331822 | A1* | 11/2016 | Hacohen | | A61P 35/02 |
| 2016/0339090 | A1* | 11/2016 | Hacohen | | C07K 16/2818 |
| 2017/0160269 | A1* | 6/2017 | Linnemann | | G01N 33/505 |
| 2017/0233821 | A1* | 8/2017 | Lianidou | | C12Q 1/6858 |
| | | | | | 435/6.11 |
| 2017/0298441 | A1* | 10/2017 | Wu | | C12Q 1/6858 |
| 2018/0000913 | A1* | 1/2018 | Hacohen | | G01N 33/5011 |
| 2018/0039726 | A1* | 2/2018 | Boissel | | G16B 5/00 |
| 2018/0055922 | A1* | 3/2018 | Hacohen | | A61K 40/42 |
| 2018/0108440 | A1* | 4/2018 | Stevens | | G16H 40/67 |
| 2018/0127803 | A1* | 5/2018 | Lei | | C12Q 1/68 |
| 2018/0153975 | A1* | 6/2018 | Fritsch | | A61K 39/001151 |
| 2018/0330824 | A1* | 11/2018 | Athey | | G16B 40/00 |
| 2019/0050534 | A1* | 2/2019 | Apte | | C12Q 1/689 |
| 2019/0060428 | A1* | 2/2019 | Fritsch | | A61P 37/02 |
| 2019/0060432 | A1* | 2/2019 | Hacohen | | A61P 35/00 |
| 2019/0096526 | A1* | 3/2019 | Hirsch | | G06N 7/01 |
| 2019/0099475 | A1* | 4/2019 | Benz | | C12N 5/0638 |
| 2019/0376147 | A1* | 12/2019 | Fritsch | | C12Q 1/6858 |
| 2020/0004751 | A1* | 1/2020 | Stennett | | G06F 16/24568 |
| 2020/0016251 | A1* | 1/2020 | Hacohen | | A61K 39/0011 |
| 2020/0069783 | A1* | 3/2020 | Hacohen | | A61K 39/0011 |
| 2020/0258601 | A1* | 8/2020 | Lau | | G16H 50/20 |
| 2020/0330571 | A1* | 10/2020 | Fritsch | | A61K 39/001191 |
| 2021/0090694 | A1* | 3/2021 | Colley | | G16B 30/00 |
| 2021/0233664 | A1* | 7/2021 | Colley | | G16H 50/70 |
| 2021/0366577 | A1* | 11/2021 | Koller | | G16B 40/20 |
| 2022/0157403 | A1* | 5/2022 | Mason | | G06N 5/022 |
| 2022/0165359 | A1* | 5/2022 | Lee | | G16B 40/20 |
| 2022/0262462 | A1* | 8/2022 | Peters | | G16B 20/00 |
| 2022/0307026 | A1* | 9/2022 | Senapathy | | G16B 45/00 |
| 2022/0310196 | A1* | 9/2022 | Polykovskiy | | G16B 20/00 |
| 2022/0310198 | A1* | 9/2022 | Collins | | G16B 35/20 |
| 2022/0310201 | A1* | 9/2022 | Senapathy | | G16H 20/10 |
| 2022/0310274 | A1* | 9/2022 | Senapathy | | G16H 15/00 |
| 2022/0310275 | A1* | 9/2022 | Senapathy | | G16B 45/00 |
| 2022/0316009 | A1* | 10/2022 | Senapathy | | G16B 30/00 |
| 2022/0375611 | A1* | 11/2022 | Gates | | G16H 50/20 |
| 2023/0122305 | A1* | 4/2023 | Senapathy | | G16B 20/10 |
| | | | | | 435/6.11 |
| 2023/0148855 | A1* | 5/2023 | Wang | | G06T 7/0016 |
| | | | | | 382/128 |
| 2023/0154567 | A1* | 5/2023 | Senapathy | | G16B 30/10 |
| | | | | | 702/20 |
| 2023/0154580 | A1* | 5/2023 | Wang | | A61B 1/31 |
| | | | | | 382/118 |
| 2023/0170057 | A1* | 6/2023 | Kozloski | | G06N 3/08 |
| | | | | | 702/19 |
| 2023/0223121 | A1* | 7/2023 | Colley | | G16B 30/00 |
| | | | | | 705/2 |
| 2023/0245788 | A1* | 8/2023 | Colley | | G16H 20/00 |
| | | | | | 702/19 |
| 2023/0368915 | A1* | 11/2023 | Abraham | | G01N 33/574 |
| 2023/0420143 | A1* | 12/2023 | Buckler | | G16H 50/50 |
| 2024/0112752 | A1* | 4/2024 | Patwardhan | | G16B 50/10 |
| 2024/0161017 | A1* | 5/2024 | Pisner | | G16H 50/20 |
| 2024/0194299 | A1* | 6/2024 | Garcia | | G16B 40/20 |
| 2024/0289586 | A1* | 8/2024 | Balakrishnan | | G06N 3/098 |
| 2024/0303544 | A1* | 9/2024 | Baranzini | | G06N 5/022 |
| 2024/0312581 | A1* | 9/2024 | Colley | | G16H 20/10 |
| 2024/0344138 | A1* | 10/2024 | Benjamin | | A61K 39/0011 |
| 2024/0390497 | A1* | 11/2024 | Richards | | A61K 40/11 |
| 2024/0404640 | A1* | 12/2024 | Schaffer | | G16B 40/20 |
| 2025/0125054 | A1* | 4/2025 | Muhammad | | G16B 20/00 |
| 2025/0182848 | A1* | 6/2025 | Catterson | | G06N 3/08 |
| 2025/0186406 | A1* | 6/2025 | Zarrinpar | | A61K 31/436 |
| 2025/0210196 | A1* | 6/2025 | Frieder | | G06N 20/10 |

OTHER PUBLICATIONS

Auwerx, HGG Advances, 2022, pp. 1-24.*
Azizi, CellPress, 2018 pp. 1293-1308.*
Chalancon, 2012, 2012 pp. 21-32.*
Dijik, CellPress, 2018, pp. 716-729.*
Herholt, Elsevier, 2020, pp. 18-35.*
Huang, CellPress, pp. 1-29.*
Kapoor, 2016, Elsevier, pp. 3232-3245.*
Karaca, 2018, Genetics in Medicine, pp. 28-37.*
Kashyap, CellPress, 2022, pp. 647-676.*
Knight, CellPress, 2022, pp. 916-938.*
Kriete, Computational Systems Biology, 2010, Chapter 14.*
Lee, Elsevier, 2017, pp. 118-123.*
Li, Elsevier, 2022, pp. 1-20.*

(56) References Cited

OTHER PUBLICATIONS

Lötsch, Elsevier, 2013, pp. 21-28.*
Masoudi-Sobhanzadeh, Elsevier, 2019, pp. 254-262.*
Nickel, Elsevier, 2015, pp. 126-142.*
Parisi, Elsevier, 2020, pp. 1043-1055.*
Perera, 2010, Elsevier, Chapter 22.*
Prasad, Elsevier, 2022, Chapter 21.*
Razo-Mejia, CellPress, 2018, pp. 56-69.*
Schirle, Elsevier, 2016, pp. 82-89.*
She, Elsevier, 2018, pp. 478-490.*
Sina, CellPress, 2019, pp. 955-966.*
Smart, CellPress, Feb. 2023, pp. 1-23.*
Tan, Elsevier, Jan. 2023, pp. 61-75.*
Vukoviv, Elsevier, 2018, pp. 58-66.*
Wellenreuther, CellPress, 2016, pp. 155-164.*

Wilard & Ginsburg, Genomic-and-Personalized-Medicine, Elsevier, 2009, Chapter 3.*
Wooten, Elsevier, 2017, 167-175.*
Xu, Elsevier, 2021, pp. 1-9.*
Zabinsky, Elsevier, 2019, pp. 21-35.*
Zitnik_Elsevier_2028_pp. 71-91.*
Gómez-Echavarría, Elsevier, 2020, pp. 1081-1093.*
Bueschbell, Elsevier, 2022, pp. 1-26.*
Park et al., 2022, Cell Genomics, pp. 1-e11.*
Dannenfelser_et_al._2020_Cell_Systems_11_pp. 215-228.*
Goulet_Elsevier_2020_pp. 74-103.*
Lim_Cell_2017_pp. 724-740.*
Robertson_J._Biol._Chem._2020_pp. 18436-18448.*
Zabel_Elsevier_2019_pp. 53-69.*
Tian_et_al, Elsevier, Oct. 2023, pp. 1-e7.*

* cited by examiner

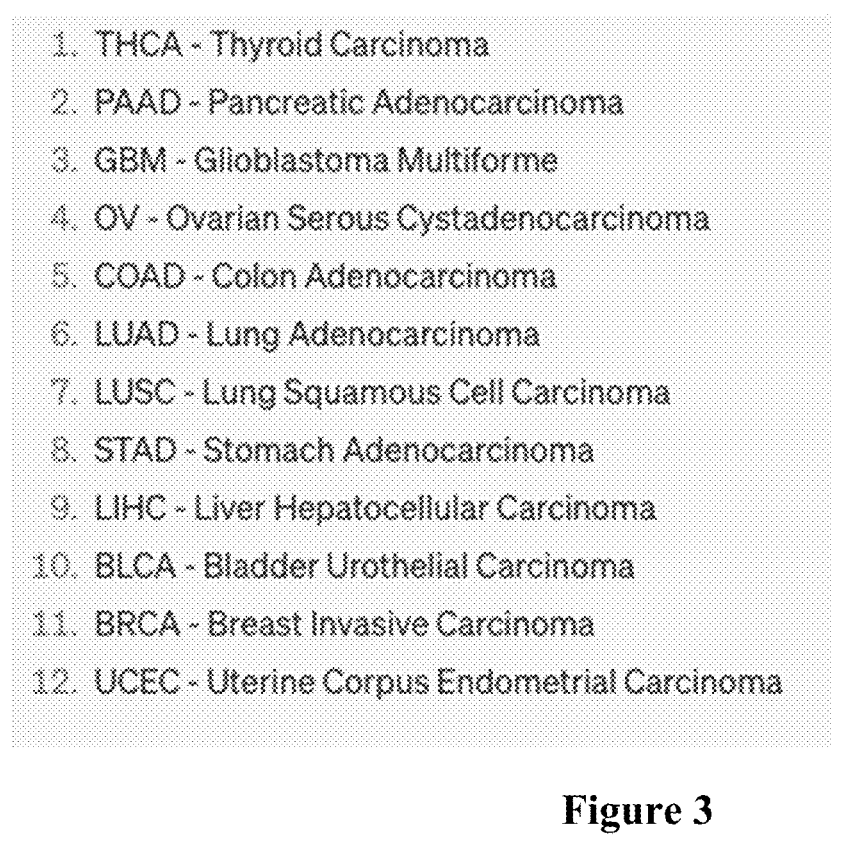

1. THCA - Thyroid Carcinoma

2. PAAD - Pancreatic Adenocarcinoma

3. GBM - Glioblastoma Multiforme

4. OV - Ovarian Serous Cystadenocarcinoma

5. COAD - Colon Adenocarcinoma

6. LUAD - Lung Adenocarcinoma

7. LUSC - Lung Squamous Cell Carcinoma

8. STAD - Stomach Adenocarcinoma

9. LIHC - Liver Hepatocellular Carcinoma

10. BLCA - Bladder Urothelial Carcinoma

11. BRCA - Breast Invasive Carcinoma

12. UCEC - Uterine Corpus Endometrial Carcinoma

Figure 3

| LogFC_mean | dependency_mean | gene_symbols | percentile | ab_avail_1 | ab_avail_2 | max_tissue | max_tissue_tissue |
|---|---|---|---|---|---|---|---|
| 5.439610873 | -0.019806174 | CLDN18,CDH3 | 0.01058022 | TRUE | TRUE | 2.26217 | Testis |
| 4.808959601 | -0.016675607 | CLDN18,GPR35 | 0.08887384 | TRUE | TRUE | 4.79128 | Stomach |
| 4.809646492 | -0.037666013 | CLDN18,FAP | 0.1206145 | TRUE | TRUE | 5.86088 | Lung |
| 4.331034304 | -0.047762515 | CLDN18,MET | 0.14177494 | TRUE | TRUE | 9.77375 | Lung |
| 3.900485002 | -0.019443523 | CLDN18,CLDN1 | 0.14389098 | TRUE | TRUE | 8.56398 | Lung |
| 4.034840021 | -0.027104984 | CA9,TM4SF5 | 0.27296966 | TRUE | TRUE | 7.06972 | Stomach |
| 4.434022418 | -0.004938153 | CLDN18,LY75 | 0.29201405 | TRUE | TRUE | 6.68719 | Lung |
| 4.443724047 | -0.016314372 | CLDN18,APLNR | 0.36395954 | TRUE | TRUE | 3.84176 | Lung |
| 4.110053168 | -0.014075896 | CLDN18,SLAMF7 | 0.53535909 | TRUE | TRUE | 7.75084 | Lung |
| 3.967885016 | -0.030618097 | CLDN18,ROR2 | 0.56286766 | TRUE | TRUE | 8.19141 | Lung |
| 3.993911714 | -0.074098239 | CLDN18,CD27 | 0.65385755 | TRUE | TRUE | 4.82068 | Lung |
| 3.796915125 | -0.037109802 | CLDN18,IYD | 0.70252656 | TRUE | TRUE | 0.461527 | Thyroid |

Figure 4

| LogFC_mean | dependency_mean | gene_symbols | percentile | ab_avail_1 | ab_avail_2 | max_tissue_exp | max_tissue_tissue |
|---|---|---|---|---|---|---|---|
| 5.33077338 | -0.072670691 | CLDN18,DUOX2 | 0 | TRUE | FALSE | 9.83001 | Stomach |
| 4.995313325 | -0.118534915 | TSPAN1,TM4SF4 | 0.002116044 | FALSE | FALSE | 8.99085 | Small_Intestine_Terminal_Ileum |
| 5.595461635 | -0.111199264 | TSPAN1,GJB3 | 0.004232088 | FALSE | FALSE | 9.19894 | Vagina |
| 5.233983223 | -0.047229465 | CLDN18,AQP5 | 0.006348132 | TRUE | FALSE | 8.83962 | Stomach |
| 4.681518029 | -0.080407505 | CLDN18,TM4SF4 | 0.008464175 | TRUE | FALSE | 3.72515 | Stomach |
| 5.439610873 | -0.019806174 | CLDN18,CDH3 | 0.010580219 | TRUE | TRUE | 2.26217 | Testis |
| 5.198159597 | -0.074329696 | CLDN18,DUOXA2 | 0.012696263 | TRUE | FALSE | 3.65514 | Stomach |
| 4.804276296 | -0.056365966 | DUOXA2,TMC5 | 0.014812307 | FALSE | FALSE | 3.65514 | Stomach |
| 5.165616182 | -0.006619408 | CLDN18,GABRP | 0.016928351 | TRUE | FALSE | 0.751074 | Pituitary |
| 4.935890059 | -0.060657961 | DUOX2,TMC5 | 0.019044395 | FALSE | FALSE | 9.83001 | Stomach |
| 4.771048668 | -0.09665913 | DUOX2,TSPAN8 | 0.021160438 | FALSE | FALSE | 9.83001 | Stomach |
| 4.727540105 | -0.095404988 | DUOX2,PIGR | 0.023276482 | FALSE | FALSE | 9.83001 | Stomach |
| 4.959534532 | 0.103041473 | VSIG2,TM4SF5 | 0.025392526 | FALSE | TRUE | 9.14044 | Colon_Transverse |
| 4.258350914 | -0.10347601 | FXYD5,TM4SF4 | 0.02750867 | FALSE | FALSE | 8.99085 | Small_Intestine_Terminal_Ileum |
| 5.074725319 | -0.020023305 | DUOX2,IL2RG | 0.029624614 | FALSE | FALSE | 9.54812 | Esophagus_Mucosa |
| 4.656185587 | 0.000311184 | VSIG2,TM4SF4 | 0.031740658 | FALSE | FALSE | 3.72515 | Stomach |
| 4.687772997 | -0.085099124 | TMC5,GJB3 | 0.033856702 | FALSE | FALSE | 4.52754 | Prostate |
| 4.528824545 | -0.045892332 | CLDN18,AMN | 0.035972746 | TRUE | FALSE | 6.24652 | Lung |
| 4.636434873 | -0.092317135 | DUOXA2,TSPAN8 | 0.038088789 | FALSE | FALSE | 6.45311 | Thyroid |
| 4.984897014 | 0.023322803 | CLDN18,TM4SF5 | 0.040204833 | TRUE | TRUE | 7.06972 | Stomach |
| 4.613901855 | 0.019289732 | CLDN18,KCNK1 | 0.042320877 | TRUE | FALSE | 7.68193 | Stomach |
| 4.907794279 | -0.083729741 | GABRP,DUOXA2 | 0.044436921 | FALSE | FALSE | 7.43079 | Vagina |
| 5.025808289 | -0.014424468 | IL2RG,GJB3 | 0.046552965 | FALSE | FALSE | 9.54812 | Esophagus_Mucosa |
| 4.287634706 | -0.052434775 | TMC5,TM4SF4 | 0.048669008 | FALSE | FALSE | 6.99085 | Small_Intestine_Terminal_Ileum |
| 4.6809663 | -0.603014052 | TSPAN1,FCGR1A | 0.050788052 | FALSE | FALSE | 5.5539 | Lung |
| 4.881586896 | -0.086916509 | CDH3,DUOXA2 | 0.052901096 | TRUE | FALSE | 7.43079 | Vagina |
| 4.942111582 | -0.01566131 | DUOXA2,IL2RG | 0.055017114 | FALSE | FALSE | 7.43079 | Vagina |
| 5.31249745 | -0.040465274 | CLDN18,GJB2 | 0.057133184 | TRUE | FALSE | 2.29562 | Testis |
| 4.676523072 | -0.089808151 | PIGR,GJB3 | 0.059249228 | FALSE | FALSE | 3.70291 | Prostate |
| 4.595026329 | -0.091082993 | DUOXA2,PIGR | 0.061365271 | FALSE | FALSE | 3.65514 | Stomach |
| 4.675959313 | -0.0943398 | AQP5,DUOXA2 | 0.063481315 | FALSE | FALSE | 7.28803 | Esophagus_Mucosa |
| 4.559486895 | -0.029129527 | DUOX2,TM4SF5 | 0.065597359 | FALSE | TRUE | 7.06972 | Stomach |
| 4.808873124 | -0.098681794 | AQP5,DUOX2 | 0.067713403 | FALSE | FALSE | 8.83637 | Skin_Not_Sun_Exposed_Suprapubic |
| 4.255107851 | -0.131859835 | DUOX2,TM4SF4 | 0.069829447 | FALSE | FALSE | 3.72515 | Stomach |
| 4.789625437 | 0.02143094 | CLDN18,CEACAM1 | 0.071945491 | TRUE | TRUE | 8.86503 | Lung |

Figure 9

| Cancer | Suitability Score | Gene Target Pairs | Cancer | Suitability Score | Gene Target Pairs |
|---|---|---|---|---|---|
| Ovarian cancer | 0.08623772239 | EPCAM,MUC16 | Pancreatic ductal adenocarcinoma | 0.1361008145 | CLDN18,CDH3 |
| | 0.1203670028 | MUC1,MUC16 | | 0.177575088 | CLDN18,CEACAM1 |
| | 0.1424245245 | TNFRSF12A,MUC16 | | 0.18729089 | CLDN18,MET |
| | 0.1497965369 | ERBB3,MUC16 | | 0.1886877217 | CLDN18,FAP |
| | 0.1556356469 | CDH6,MUC16 | | 0.1894864969 | CLDN18,GPR35 |
| | 0.1618161219 | CXCR4,MUC16 | | | |
| | 0.1635023193 | CDH6,EPCAM | Breast cancer | 0.02307865595 | EPCAM,PRLR |
| | 0.1693443197 | CD74,MUC16 | | 0.02944403426 | CDH1,PRLR |
| | 0.1801704915 | SDC1,MUC16 | | 0.03598716846 | PRLR,TACSTD2 |
| | 0.1811698692 | SORT1,MUC16 | | | |
| | 0.1825485565 | CLDN1,MUC16 | Uterine corpus endometrial carcinoma | 0.07354157194 | EPCAM,MUC16 |
| | 0.1964760388 | CD47,MUC16 | | 0.1194900552 | CDH1,MUC16 |
| | | | | 0.127857922 | TACSTD2,MUC16 |
| Colon adenocarcinoma | 0.1631506952 | CDH3,GUCY2C | | 0.1358232546 | SLC34A2,MUC16 |
| | 0.164864519 | CDH3,TM4SF5 | | 0.1492355542 | VTCN1,MUC16 |
| | 0.1805861638 | CLDN1,GUCY2C | | 0.1524968054 | SDC1,MUC16 |
| | | | | 0.1642465879 | MUC16,MUC1 |
| Head and neck squamous cell carcinoma | 0.1937067928 | CA9,HAS3 | | 0.1783465782 | ERBB3,MUC16 |
| | 0.2286802196 | CA9,ITGB6 | | | |
| | 0.2682076417 | CA9,NRP2 | | | |
| | 0.2766898594 | NETO2,GJB3 | | | |
| | 0.2812350277 | NETO2,GJB5 | | | |
| | 0.3047178238 | GPR87,NETO2 | | | |

Figure 19

SYSTEMS, METHODS AND COMPUTER-ACCESSIBLE MEDIUM FOR IDENTIFYING TARGET PAIRS FOR CAR-T THERAPY

CROSS REFERENCE TO RELATED APPLICATION(S)

This application relates to U.S. Provisional Patent Application Ser. No. 63/547,619, filed on Nov. 7, 2023, the entire disclosure of which is incorporated herein by reference.

FIELD OF THE DISCLOSURE

The present disclosure relates to identification of target pairs for various therapies, and in particular to exemplary systems, methods and computer-accessible medium that can provide exemplary procedures and/or techniques to identify AND-gated target pairs for Chimeric Antigen Receptor (CAR)-T therapy.

BACKGROUND INFORMATION

Currently, it is believed that there are no solutions for effectively identifying targets for AND gated and NOT-gated CAR-T cells and generating preclinical candidates in a scaled manner. Several AND-gated systems have been proposed (i.e., synthetic Notch receptor (LINK), synthetic Notch receptor (SynNotch) and Split CARs), and there is currently no computational tool to identify targets for AND-gated target pairs in general or any logic gated immunotherapy (ex: NOT gates).

Further, no computational tools are believed to exist that can accurately predict effective multi-target combinations for therapeutics, automatically generate CAR sequences by drawing from databases of antibodies, or which utilize Bayesian statistics to combine data covering multiple evidences correlating with clinical success including Safety, Tumor Expression, Dependency, Heterogeneity and Antibody Sequence Availability, for AND gated systems.

Thus, there is a need to address and/or improve at least these deficiencies which exist in the previous systems and methods.

SUMMARY OF EXEMPLARY EMBODIMENTS

The following is intended to be a brief summary of the exemplary embodiments of the present disclosure, and is not intended to limit the scope of the exemplary embodiments described herein.

Various deficiencies can be overcome with the exemplary systems, methods and computer-accessible medium that can provide exemplary procedures and/or techniques to identify target pairs for CAR-T therapy, in accordance with the exemplary embodiments of the present disclosure.

In some exemplary embodiments of the present disclosure, the exemplary systems, methods, and computer-accessible medium can be provided for Chimeric Antigen Receptor (CAR)-T therapy which can include selecting a first set of targets highly expressed in cancer and lowly in normal tissues, selecting a second set of targets that are highly co-expressed in the cancer and lowly in normal tissues, generating an input set by combining the first and second set of targets with dependency data, single-cell heterogencity, and antibody availability, determining, by a learning model, at least one target pair for use in CAR-T therapy, and applying a cell therapy based on the determined at least one target pair. The cell therapy can be directed toward a solid tumor. Exemplary methods, systems and computer accessible medium according to the exemplary embodiments of the present disclosure can also be provided for generating a learning model for making these target pair determinations. Such target pair(s) can be determined based on a specific type of cancer, and can be determined to distinguish healthy tissue from cancer. The target pair(s) can be determined to activate an AND-gated CAR-T cell and/or a NOT-gated CAR-T cell. Furthermore, the learning model can predict a value of the determined at least one target pair which can be based on one or more of a predicted efficacy and a predicted safety, and can be ranked against the predicted values of each of the at least one target pair.

In some exemplary embodiments of the present disclosure, the exemplary systems, methods, and computer accessible medium can be provided for automatically generating a Chimeric Antigen Receptor (CAR) sequence which can include identifying a target, selecting a scFv to clone against the identified target, selecting a configuration for the scFVs wherein the configuration is one of Variable Light (VL)-Variable Heavy (VH) and VH-VL, selecting at least one CAR domain, and generating the identified target based on the scFv, the scFv configuration, and the at least one CAR domain.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 3 is an exemplary list of cancer types supported by Logic-Finder automatic workflow according to an exemplary embodiment of the present disclosure;

FIG. 4 is a table providing an exemplary application of Logic-Finder on Pancreatic Ductal Adenocarcinoma (PDAC) according to an exemplary embodiment of the present disclosure;

FIG. 9 is an exemplary tabular view when extending the target pair list to targets with or without available Ab sequences with more targets emerging, according to an exemplary embodiment of the present disclosure;

FIG. 19 is an exemplary table providing a list of top target pairs in six labeled cancers as predicted by exemplary embodiments of the present disclosure.

Figure 1:
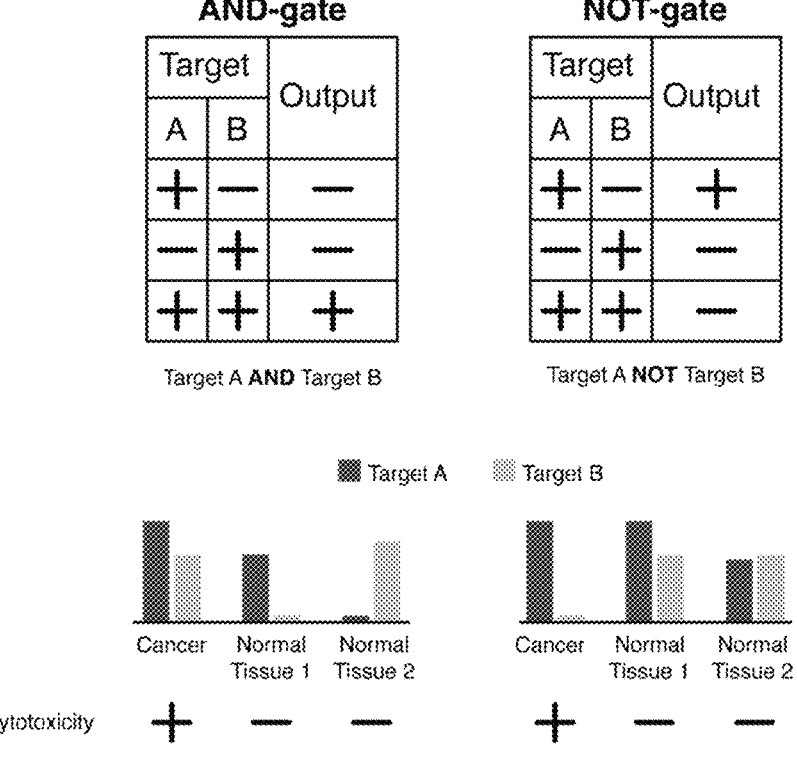
FIG. 1 is a set of exemplary representations of an exemplary AND-gated and NOT-gated CARs mode of action and charts associated therewith according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the certain exemplary embodiments illustrated in the figures and the appended claims.

DETAILED DESCRIPTION OF EXEMPLARY EMBODIMENTS

The following description of exemplary embodiments provides non-limiting representative examples referencing numerals to particularly describe features and teachings of different aspects of the present disclosure. The exemplary embodiments described should be recognized as capable of implementation separately, or in combination, with other exemplary embodiments from the description of the exemplary embodiments. A person of ordinary skill in the art reviewing the description of the exemplary embodiments should be able to learn and understand the different described aspects of the present disclosure. The description of the exemplary embodiments should facilitate understanding of the invention to such an extent that other implementations, not specifically covered but within the knowledge of a person of skill in the art having read the description of embodiments, would be understood to be consistent with an application of the exemplary embodiments of the present disclosure.

Exemplary systems, methods and computer-accessible medium according to exemplary embodiments of the present disclosure can solve one of the major challenges restricting the clinical application of CAR T cells, namely the availability of tumor-specific molecules that can be targeted safely and effectively. Optimal immunotherapy targets should be highly overexpressed in tumor cells, absent in healthy tissue, homogenously expressed in tumors, and essential to the biology of these tumors. Logic-gating enables targeting through two molecules, each of which may be expressed in healthy tissue, yet the pair is exclusively co-expressed in tumor cells. Exemplary systems, methods and computer-accessible medium according to exemplary embodiments of the present disclosure provides for identification of optimal target pairs and the generation of logic-gated CAR T constructs that can be screened in preclinical studies. Exemplary systems, methods and computer-accessible medium according to exemplary embodiments of the present disclosure can identify target pairs that will be most clinically meaningful and can generate constructs in a scaled manner such as to enable multiplexed screening of the resulting constructs. Given a specific cancer, exemplary systems, methods and computer-accessible medium according to exemplary embodiments of the present disclosure can output top scoring target pairs based on suitability of safety and efficacy.

Exemplary systems, methods and computer-accessible medium according to exemplary embodiments of the present disclosure can automatically generate DNA and/or protein sequences for logic-gated CAR T constructs in existing CAR platforms such as synNotch, LINK and split CARs. These constructs can be easily synthesized and screened using conventional CAR T cell assays. Constructs with potent on-target efficacy and lack of off-target activity can be translated into clinical studies. Exemplary systems, methods and computer-accessible medium according to exemplary embodiments of the present disclosure can significantly expand the landscape of targetable tumors and accelerate the rate of new CAR development.

According to the exemplary embodiments of the present disclosure, an appropriate or good target pair can be defined by, e.g., (1) not being expressed in normal tissues, (2) being enriched in cancer, (3) being essential for tumor growth, (4) being homogenous across diverse tumor clones, and (5) optionally if the target pair has scFv or mAb available.

The exemplary systems, methods and computer-accessible medium according to exemplary embodiments of the present disclosure can predict target pairs that are optimal for use in AND-gated Chimeric Antigen Receptor (CAR)-T Cells.

As shown in FIG. 1, an AND gated CAR-T cell has binders for two antigens and will only activate when both antigens are present on a cell. Human T-cells express T cell receptors (TCRs), which can identify foreign antigens on antigen presenting cells (APCs). Cancer cells evade endogenous TCRs, and thus traditional CARs were developed to activate when exposed to a single antigen recognized by the scFv. This has been effective for hematologic malignancies, which while eliminating the cancer, usually leads to a significant depletion of healthy cells. A single target CAR has not been found to be effective in most solid tumors due to the heterogeneity of the tumors not responding to a single target approach.

FIG. 1 shows a set of illustrations of how AND-gated and NOT-gated CAR-T would only activate when, e.g., two antigens are simultaneously presented thereto. For example, such AND-gated CAR-T would not activate if one of the target antigens is presented to it or if none of the target antigens are presented it. It requires both targets at the same time to activate the T cell. This is what facilitates the solid tumor targeting specificity. Thus, AND-gated CAR T cells avoid off-tumor toxicity by killing target cells only when there is high co-expression of both targets. For NOT-gated CARs, CAR T cells will activate only in the absence of the target B, while they will not be toxic in the presence of it. Thus, NOT-gated CAR T cells are able to be activated and kill target cells where Target B is absent or its expression is minimal. The exemplary systems, methods and computer-accessible medium according to exemplary embodiments of the present disclosure can identify these target pairs and then generate the CAR sequence to be transduced into T cells.

The exemplary systems, methods and computer-accessible medium according to exemplary embodiments of the present disclosure can be provided in Python 3, and can be broken down into, e.g., two parts—(1) data collection, and (2) predictions. According to the exemplary embodiments of the present disclosure, the data processing procedure can be provided and implemented using the software, which can be used to receive a cancer acronym as an input from the user to tell the software what cancer it should analyze. For example, the exemplary systems, methods and computer-accessible medium according to the exemplary embodiments of the present disclosure can then automatically download the differential gene expression data for that cancer from the Gene Expression Profiling Interactive Analysis (GEPIA), filter for genes that have a highly positive log fold change value that can be tuned by a user, and then possibly remove any genes with a p-value above the selected p-value from the user.

Figure 2:
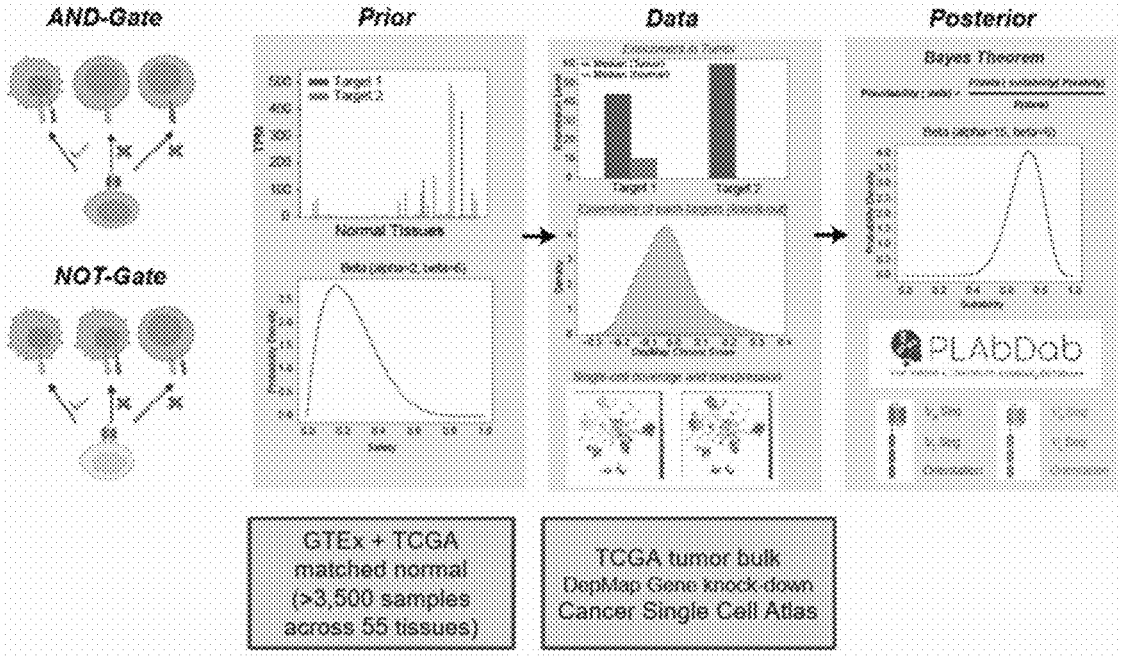
FIG. 2 is a set of exemplary illustrations of Logic-Finder—the first computational algorithm to identify target pairs in cancer and graphs associated therewith according to an exemplary embodiment of the present disclosure.

As provided in FIG. 2 which shows a set of illustrations of an exemplary overall workflow of Logic-Finder system with associated exemplary graphs according to the exemplary embodiment of the present disclosure. For example, the exemplary procedure can begin with a visual representation of an AND-gated CAR-T cell activating only when two target antigens are presented on a cell, compared to a NOT-gated CAR-T cell only activating when one target antigen is presented while the other is absent. In this exemplary embodiment of the present disclosure, the first procedure implemented in the exemplary system can include a generation of a prior distribution representing the safety profile for each target pairs by utilizing normal health tissue expression data from the Genotype-Tissue Expression Program (GTEx) and The Cancer Genome Atlas (TCGA) matched control. Next, in the second procedure, various scores ranking each individual target can be generated by pulling differential gene expression data from the Gene Expression Profiling Interactive Analysis (GEPIA). With the exemplary third procedure, dependency data from The Cancer Dependency Map Project (DepMap), and single-cell RNA-seq data from the Cancer Single-cell Expression Map (CancerSCEM). Distributions can be generated to represent each score for each target.

Figure 13:
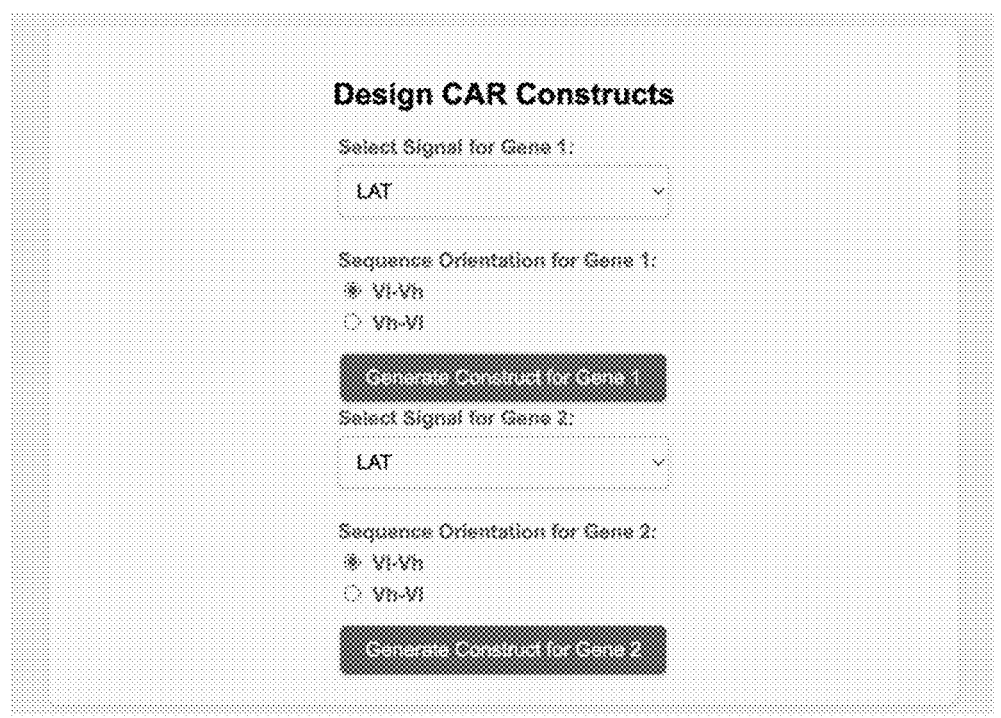
FIG. 13 is an exemplary user interface for generating CAR FASTA sequences, allowing selection of intracellular signaling domains and VL-VH order according to an exemplary embodiment of the present disclosure.

The posterior distribution can then be generated (e.g., using Bayes Theorem) to identify and prioritize the target pairs. The exemplary system, method and/or computer-accessible medium can perform at least one search to identify which target pairs has available variable heavy (VH) and variable light (VL) antibody (Ab) sequences so a CAR construct can be produced. One or more users of the exemplary systems, methods and computer-accessible medium according to exemplary embodiments of the present disclosure can then select intracellular signaling domain, and exemplary embodiments of the present disclosure can download an exemplary FASTA file of the CAR construct, as shown in FIG. 13.

FIG. 3 shows an exemplary list of cancer types supported and/or identified by Logic-Finder automatic workflow according to an exemplary embodiment of the present disclosure. For example, the exemplary Logic-Finder system and method according to the exemplary embodiments of the present disclosure can automatically collect all necessary data and predict the best target pairs for each of these cancers without any manual data input.

The exemplary systems, methods and computer-accessible medium, according to exemplary embodiments can then be used to process such data using, e.g., a Pandas DataFrame data structure, and further filter for genes that express proteins on the membrane of the cell, by using a text file that contains a list of known membrane proteins in the human cell. Various procedures that can be implemented using software, according to the exemplary embodiments of the present disclosure, can then generate a new DataFrame that contains the gene name and the ENSG identifier. At this point the software of exemplary embodiments has a list of genes that code for membrane proteins that are highly expressed in the selected cancer compared to healthy tissue. The exemplary systems, methods and computer-accessible medium the exemplary embodiments of the present disclosure can then download from GTEx the normal tissue expression data for each of these genes and compute the maximum normal tissue expression for every possible target pair combination. Thus, with the exemplary embodiments of the present disclosure, this can be facilitated by generating a list of, e.g., every possible target pair combination from the narrowed down list, finding the maximum overlapping expression in normal tissue, and then selecting the target pairs that are below a normal tissue expression threshold provided by the user.

At this point, the exemplary systems, methods and computer-accessible medium of exemplary embodiments has a list of target pairs for the AND-gated CAR that are lowly expressed in normal tissue and highly expressed in the cancer. Next, the exemplary systems, methods and computer-accessible medium, according to exemplary embodiments, can download or otherwise obtain single cell RNA-seq data for the specified cancer from the Cancer Single-cell Expression Map. Once downloaded, the exemplary systems, methods and computer-accessible medium of exemplary embodiments can extract the contents from the zip files by using the zip-file library in Python. After the data extraction, the exemplary systems, methods and computer-accessible medium according to exemplary embodiments of the present disclosure can locate the common genes present across most or all of the single cell RNA-seq data files, and then can only proceed to process the genes expressed across all of the single cell data. According to the exemplary embodiments of the present disclosure, this script can utilize single-cell RNA sequencing (scRNA-seq) data using the scanpy library in Python.

Initially, e.g., the exemplary systems, methods and computer-accessible medium according to the exemplary embodiments of the present disclosure can identify mitochondrial and malignant genes within the dataset. The exemplary systems, methods and computer-accessible medium according to exemplary embodiments of the present disclosure can then filter the data to retain only cells expressing malignant genes above a specified threshold, enhancing the focus on potential malignant cells. The script, according to the exemplary embodiments, can perform a quality control (QC) metrics calculation and identify highly variable genes (HVGs) to pinpoint genes of interest. The script, according to the exemplary embodiments, can then undergo one or more data transformation processes, including, e.g., regression of unwanted variables and data scaling to normalize the dataset. Following such exemplary procedure, the exemplary systems, methods and computer-accessible medium according to the exemplary embodiments of the present disclosure can apply dimensionality reduction techniques: Principle Component Analysis (PCA) and Uniform Manifold Approximation and Projection (UMAP), paired with Leiden clustering to group similar cells together, facilitating the identification of different cell populations based on gene expression patterns.

The script and/or other computerized procedure(s), according to the exemplary embodiments of the present disclosure, can then record a gene coverage value indicating how heterogeneous the target is across a cancer cell population. Such exemplary value can be calculated as the mean expression value of each target in the single cell dataset. Then, the exemplary procedure implemented via software that is utilized by the exemplary systems, methods and computer-accessible medium according to the exemplary embodiments of the present disclosure can also calculate or otherwise determine a score for each target pair that indicates the co-expression of the target pair across the single cell data. For example, the exemplary software can calculate (total cells with both targets expresses)/(total cells with one target expressed). Next, the exemplary systems, methods and computer-accessible medium can download or otherwise obtain cancer gene dependency data from DepMap.

The exemplary procedures implemented via software of the exemplary systems, methods and computer-accessible medium can download the cell line dependency data for all of the cell lines for the chosen cancer, put the data into a Pandas DataFrame, and save or otherwise record such data as a CSV file. Further, the exemplary systems, methods and computer-accessible medium according to the exemplary embodiments can create or otherwise provide a DataFrame that has antibody availability status for each target pair. The exemplary software implemented via software of the exemplary systems, methods and computer-accessible medium can download the data from The Patent and Literature Antibody Database (PLAbDab). Further, e.g., at the end of the data collection procedure(s), the exemplary software according to the exemplary embodiments of the present disclosure can have this data for each target pair—log fold change, normal tissue maximum expression, single cell heterogeneity, single cell co-expression, gene dependency, and antibody status. The exemplary software of the exemplary embodiments can then run this data through the prediction scripts according to exemplary embodiments, which can be written in, e.g., Python or in any other applicable programming script.

The exemplary systems, methods and computer-accessible medium according to the exemplary embodiments of the present disclosure can leverage Bayesian statistics for this next step. Exemplary embodiments can generate one more score using BayesTS, which also uses Bayesian statistics and can create a safety score for each target pair that can be used as the prior knowledge in the next Bayesian statistics steps. The exemplary systems, methods and computer-accessible medium can feed the log fold change, dependency, and single cell heterogeneity scores into the Bayesian model. Further, according to the exemplary embodiments of the present disclosure, implemented via software of the exemplary systems, methods and computer-accessible medium can generate Model and Guide functions for each data type using the Pyro programming library.

Within the exemplary code, the exemplary systems, methods and computer-accessible medium can utilize, e.g., Beta distributions to represent each model. For log fold change for the initial data, the exemplary systems, methods and computer-accessible medium according to the exemplary embodiments of the present disclosure can create a normal distribution with a center at the median log fold change value and a standard deviation of 0.5, and then generate 100 samples from this distribution. For the dependency scores, the exemplary systems, methods and computer-accessible medium according to the exemplary embodiments of the present disclosure can collect the experimental dependencies measurement from cell line of the queried cancer types represented as a numerical list.

The single cell coverage data distribution can be simulated as a normal distribution centered at the mean expression value defined above with a standard deviation of about 0.5. 100 samples are drawn from such normal distribution for Bayesian inference process. Stochastic Variational Inference (SVI) can be used to optimize the Bayesian model, estimating the true posterior distribution by iteratively adjusting model parameters to minimize the Evidence Lower Bound (ELBO) loss. Each data type-dependency, log fold change, and single cell coverage—can be represented by an individual Bayesian model that generates a posterior distribution based on its specific characteristics and relevance to the CAR-T target prediction.

In the integration procedure, the exemplary systems, methods and computer-accessible medium according to the exemplary embodiments of the present disclosure can combine the individual posterior distributions for each data type using weighted parameters (wa, wb, wc) to balance the influence of each data type based on its modality. Such exemplary integrated Bayesian model can be used to process the combined posterior distributions to produce a single, unified posterior, which can quantify the overall suitability of each target pair. This suitability score generated by exemplary systems, methods and computer-accessible medium according to the exemplary embodiments of the present disclosure reflects the likelihood that the target pair meets the necessary safety and efficacy thresholds for AND-gated CAR-T therapy, prioritizing target pairs with the highest predicted clinical relevance and lowest off-target risks. This can be the pipeline for the AND-gated targeting of exemplary systems, methods and computer-accessible medium according to the exemplary embodiments of the present disclosure. The same and/or similar configurations and/or procedures can be used by the exemplary systems, methods and computer-accessible medium according to the exemplary embodiments of the present disclosure in conjunction with any logic gate (for example, a NOT gate), by just switching the logic gate for the expression profile.

Figure 5:
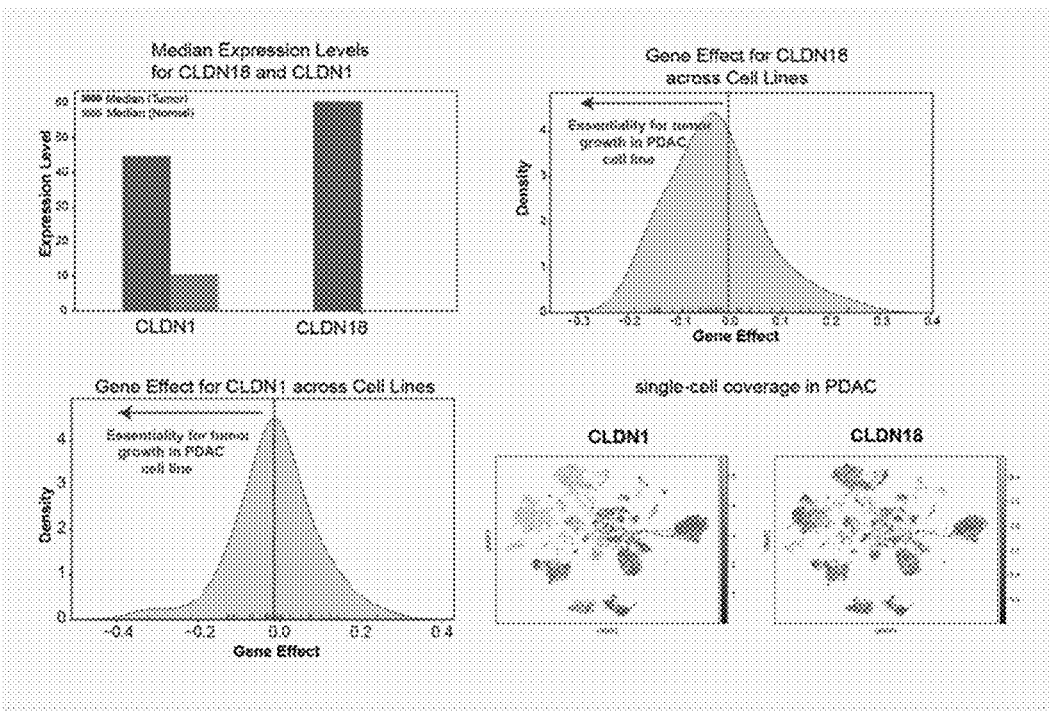
FIG. 5 is a set of exemplary graphs and plots of CLDN18.2-CLDN1 according to an exemplary embodiment of the present disclosure.
Figure 12:
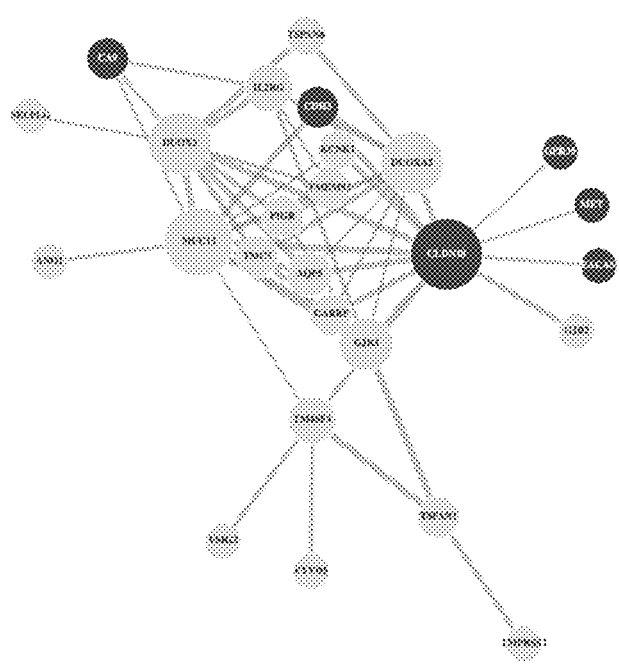
FIG. 12 is an exemplary the network plot generated for a user after a prediction is run, where each graph node represents a target and the lines between nodes indicate a viable target pair according to an exemplary embodiment of the present disclosure.

FIG. 12 shows a network plot generated by the exemplary systems, methods and computer-accessible medium according to the exemplary embodiments of the present disclosure for the top target pairs once each target pair has a suitability score generated. For example, each circle is indicative of a graph node that represents a target, indicated by the text inside in the circle. A line between two nodes indicates that it is a viable target pair. A light grey node indicates there is no antibody available and a dark grey node indicates there is an antibody sequence available. The thickness of the edges can represent the suitability of the target pair, and the thickness of the circles can indicate how many target pairs that individual target appears in. For example, the thicker the line is between two targets the better score the Bayesian model assigned to that target pair. The exemplary systems, methods and computer-accessible medium according to the exemplary embodiments of the present disclosure allow clicking on an edge between a target pair and exemplary embodiments of the present disclosure can generate a HTML webpage including the graphs in FIG. 5 showing cell lines expressing both targets in the desired cancer acquired through DepMap as indicated herein.

FIG. 13 illustrates an exemplary user interface utilized by the exemplary systems, methods and computer-accessible medium according to the exemplary embodiments of the present disclosure, where a user can select intracellular signaling domain and download the FASTA file if there is an available scFv sequence. This exemplary interface can be displayed or otherwise provided on, e.g., a web page or a mobile device by the exemplary systems, methods and computer-accessible medium according to the exemplary embodiments of the present disclosure after a user selects a target pair. For example, any target pair that has an available antibody sequence, allows this tool to generate a CAR construct and lets the user download the FASTA file.

Figure 14:
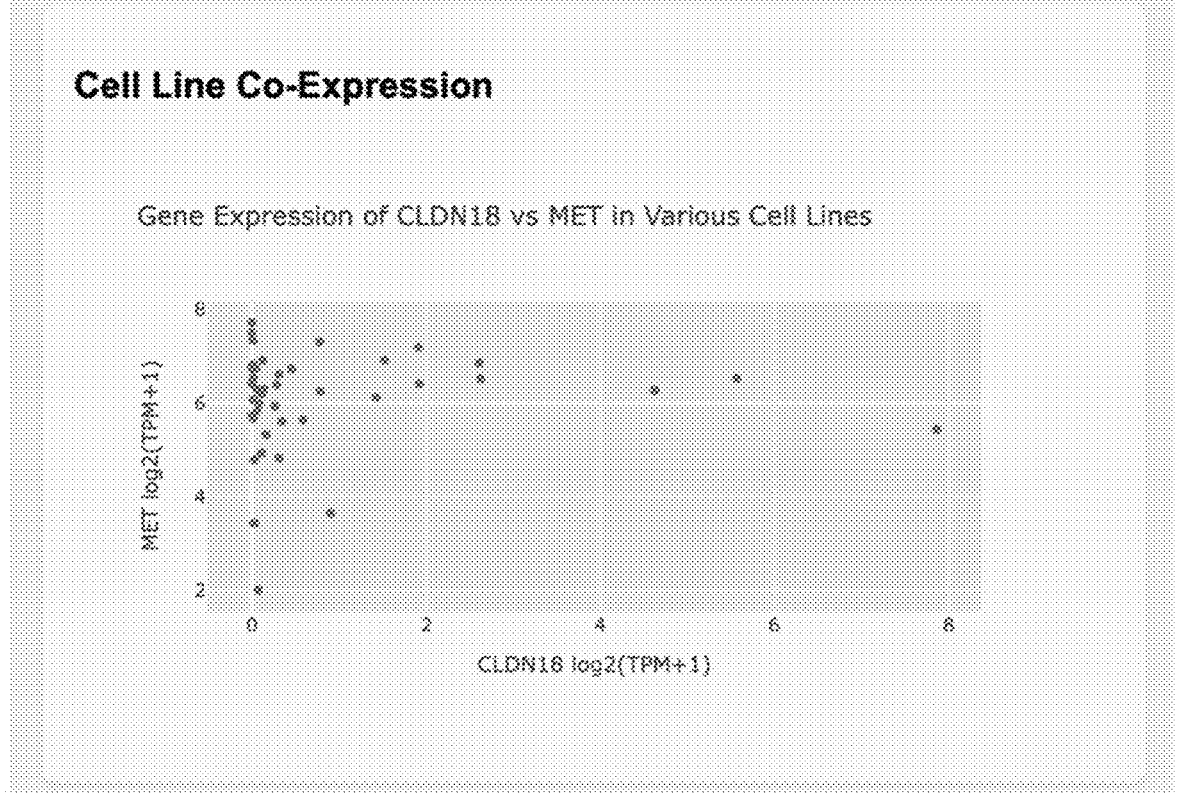
FIG. 14 is an exemplary graph of cell lines available for testing CAR constructs according to an exemplary embodiment of the present disclosure.

FIG. 14 shows an exemplary plot the can be generated by the exemplary systems, methods and computer-accessible medium according to the exemplary embodiments of the present disclosure when a user selects a target pair. For example, the exemplary systems, methods and computer-accessible medium can use data from DepMap to display cell lines that have co-expression of the predicted/selected targets. This can facilitate the user to quickly find a cell line that can be used to experimentally test the CAR construct generated by the exemplary systems, methods and computer-accessible medium according to the exemplary embodiments of the present disclosure.

Figure 15:
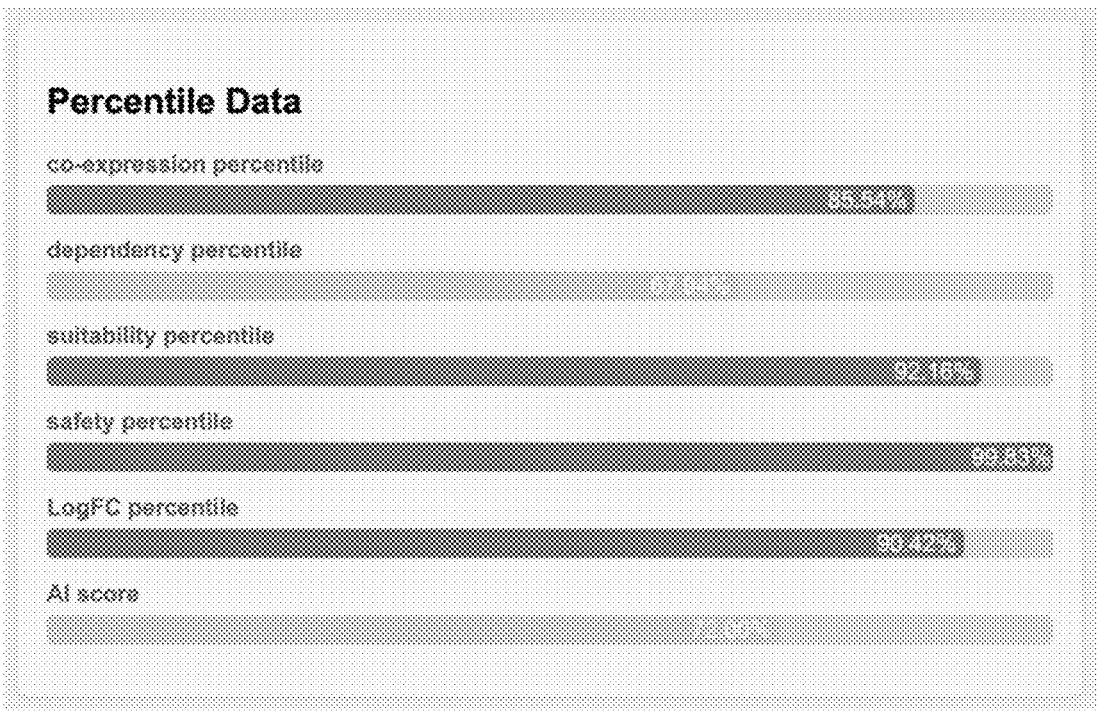
FIG. 15 is an exemplary graph highlighting scoring data across all target pairs for a chosen cancer according to an exemplary embodiment of the present disclosure.

FIG. 15 illustrates a set of exemplary charts and other associated information that can be displayed to the user once the user selects a desired target pair from the exemplary network plot shown in FIG. 12. The exemplary systems, methods and computer-accessible medium according to the exemplary embodiments of the present disclosure can calculate the percentile a target pair is in for each score generated during the prediction (co-expression, dependency, suitability, safety, log fold change, AI score). The exemplary AI score can be a score generated using OpenAI's Large Language Model (LLM) API. Exemplary systems, methods and computer-accessible medium according to the exemplary embodiments of the present disclosure can use the LLM to give a numeric prediction of how well the target pair will perform for the specified cancer in order to give the user a qualitative score of the target pair.

FIGS. 5-7 and 12-15 show exemplary illustrations that can be displayed or otherwise provided (one, some or all) to the user by the exemplary systems, methods and computer-accessible medium according to the exemplary embodiments of the present disclosure after predictions are completed to facilitate the user to select the best target pairs for testing. These graphics can be automatically generated by exemplary systems, methods and computer-accessible medium according to the exemplary embodiments of the present disclosure for every target pair and can be downloaded by the user for later reference.

FIG. 4 shows an illustration of an exemplary table providing an exemplary application of Logic-Finder on Pancreatic Ductal Adenocarcinoma (PDAC) according to an exemplary embodiment of the present disclosure. For example, column 1 of the table of FIG. 4 shows the Log Fold Change $$LFC = \log_2\left(\frac{\text{median(tumors)}}{\text{median(controls)}}\right)$$

between the two targets in each row. Column 2 of FIG. 4 shows an exemplary dependency score mean between the two targets in each row. Column 3 of FIG. 4 shows two exemplary targets (making predicted target pair) that each of scores in that row are scoring. Column 4 of FIG. 4 shows an exemplary overall percentile when comparing all predicted target pairs for PDAC. Columns 5 and 6 of FIG. 4 show an exemplary Ab availability for their respective antigen. Column 7 of FIG. 4 shows an exemplary maximum normal tissue expression of the target pair when targeted through a AND-gated system. Column 8 of FIG. 4 shows which normal tissue the highest expression is in.

FIG. 5 shows a series of exemplary graphs and plots of CLDN18.2-CLDN1 according to the exemplary embodiments of the present disclosure. For example, the median expression in Transcripts Per Million (TPM) for CLDN18 and CLDN1 are illustrated in FIG. 5. In particular, a rug plot is provided showing the dependency of PDAC on CLDN18 and CLDN1. Further, a single-cell RNA-seq expression UMAP is shown in FIG. 5 for CLDN18 and CLDN1.

Figure 6:
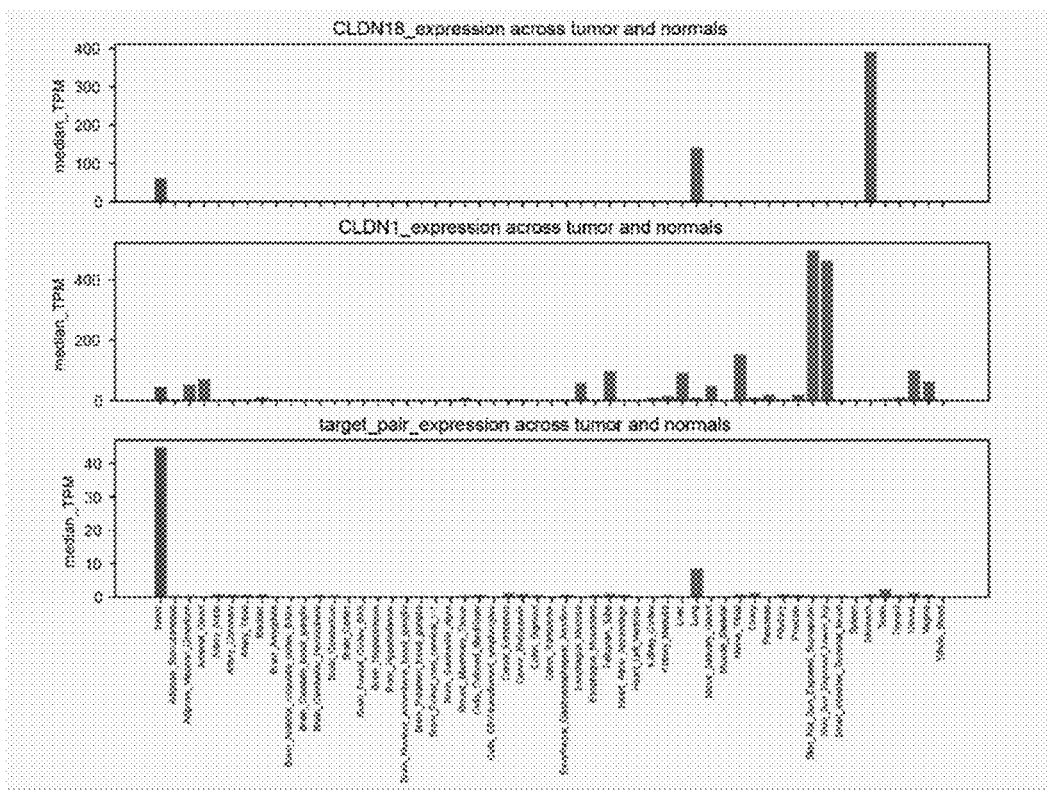
FIG. 6 is a set of exemplary graphs illustrating a comparison of therapeutic windows between single target and target pair according to an exemplary embodiment of the present disclosure.
Figure 7:
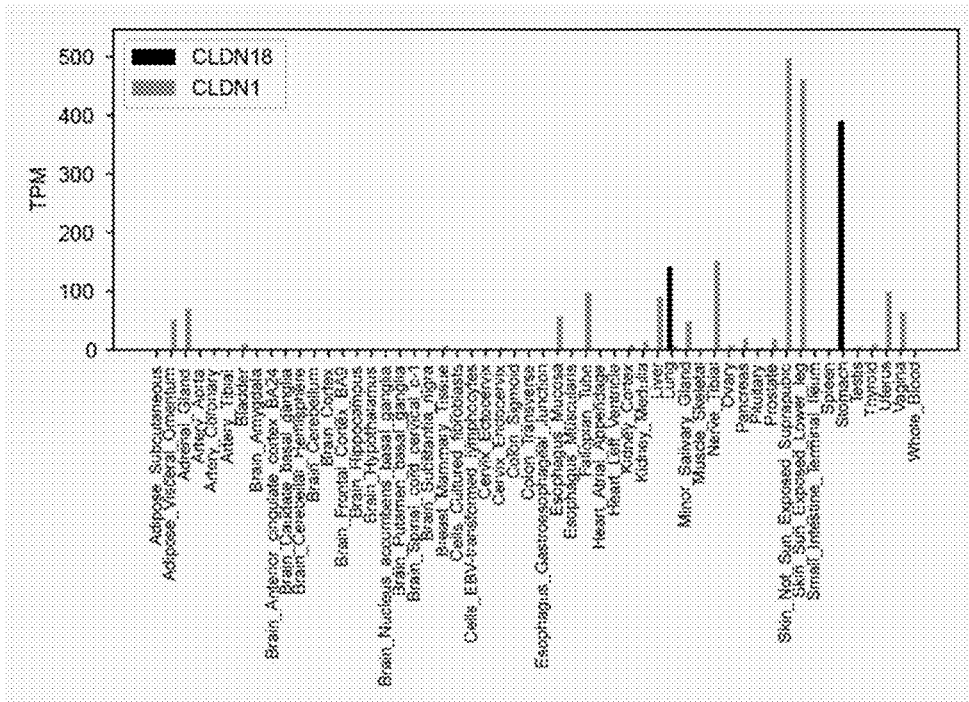
FIG. 7 is an exemplary graph of a Normal Tissue Expression according to an exemplary embodiment of the present disclosure.

FIG. 6 shows a series of exemplary graphs illustrating a comparison of therapeutic windows between single target and target pair according to an exemplary embodiment of the present disclosure. FIG. 7 illustrates an exemplary graph of a Normal Tissue Expression according to an exemplary embodiment of the present disclosure. For example, the graph of FIG. 6 generated by the exemplary Logic-Finder system according to the exemplary embodiments of the present disclosure shows the median expression for CLDN18 and CLDN1 which are illustrated in each 54 normal tissues provided by the GTEx database, according to an exemplary embodiment of the present disclosure.

Figure 8:
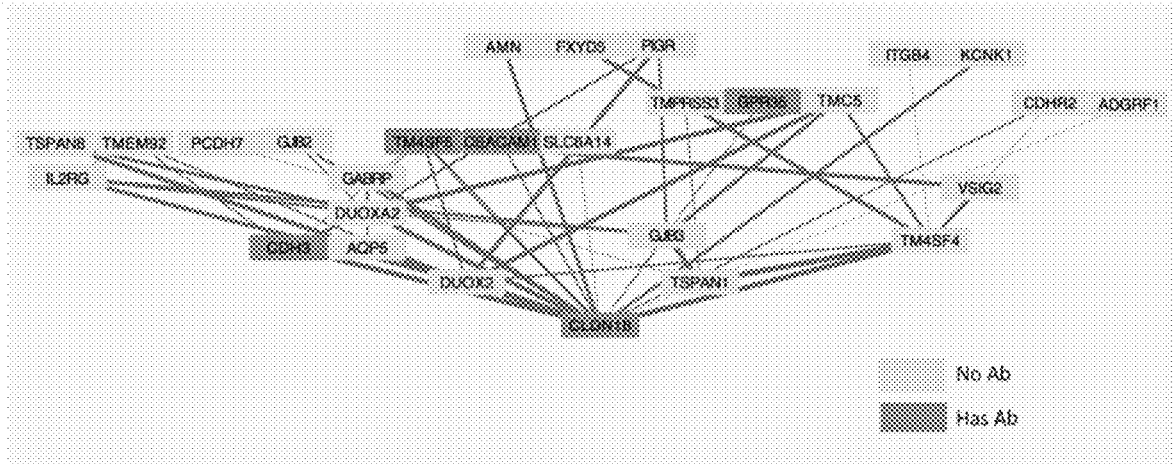
FIG. 8 is an exemplary network view when extending the target pair list to top 50 target pairs with the antibody availability information shown in distinctive node color, according to an exemplary embodiment of the present disclosure.
Figure 10:
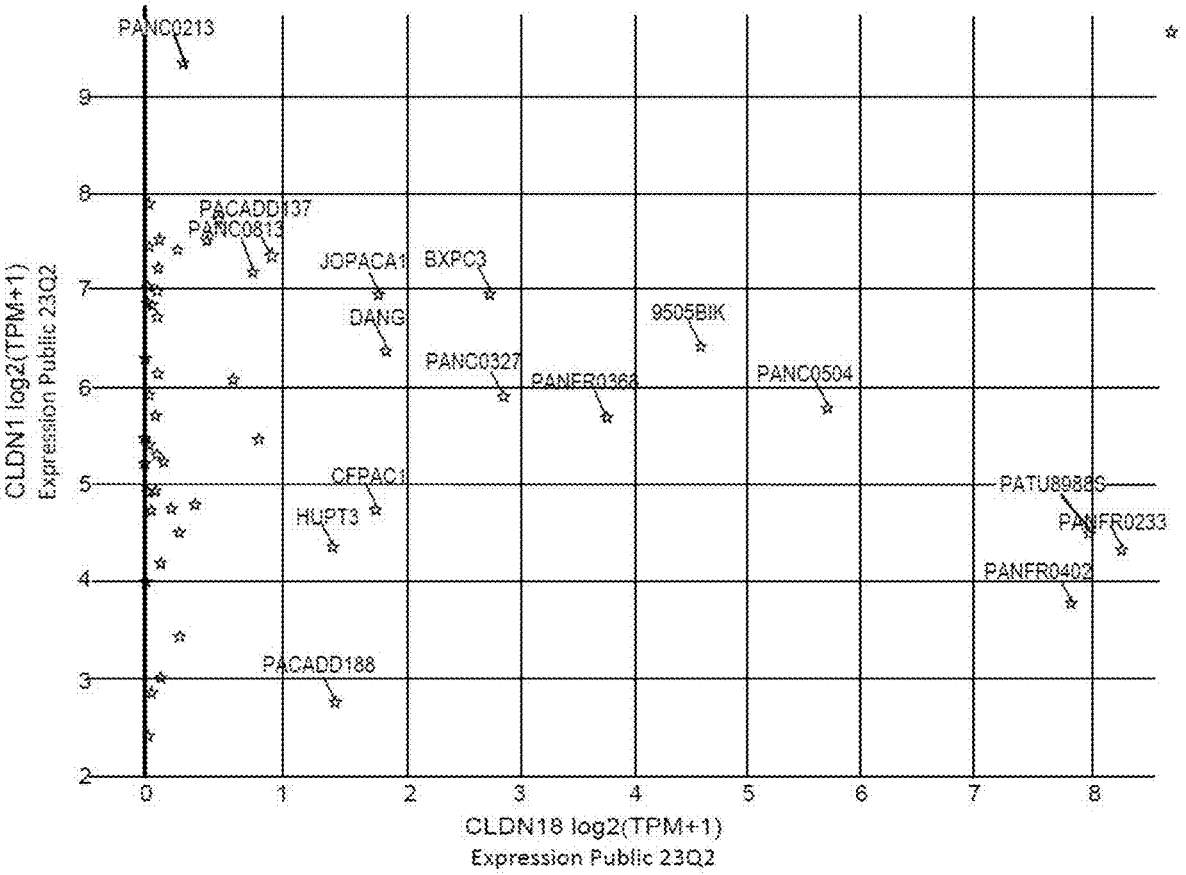
FIG. 10 is an exemplary plot of a CLDN18-CLDN1 experimental validation plan according to another exemplary embodiment of the present disclosure.

FIG. 8 shows an exemplary network view when extending the target pair list to top 50 target pairs with the antibody availability information shown in distinctive node color, according to an exemplary embodiment of the present disclosure. FIG. 9 illustrates an exemplary table for when the target pair list is extended to targets with or without available Ab sequences, e.g., with more targets emerging, according to an exemplary embodiment of the present disclosure. FIG. 10 shows an exemplary plot of a CLDN18-CLDN1 experimental validation plan according to another exemplary embodiment of the present disclosure. As shown in FIG. 10, e.g., an exemplary plots co-expression of CLDN18 and CLDN1 in cell lines (e.g., data sources from DepMap) are provided.

Figure 11:
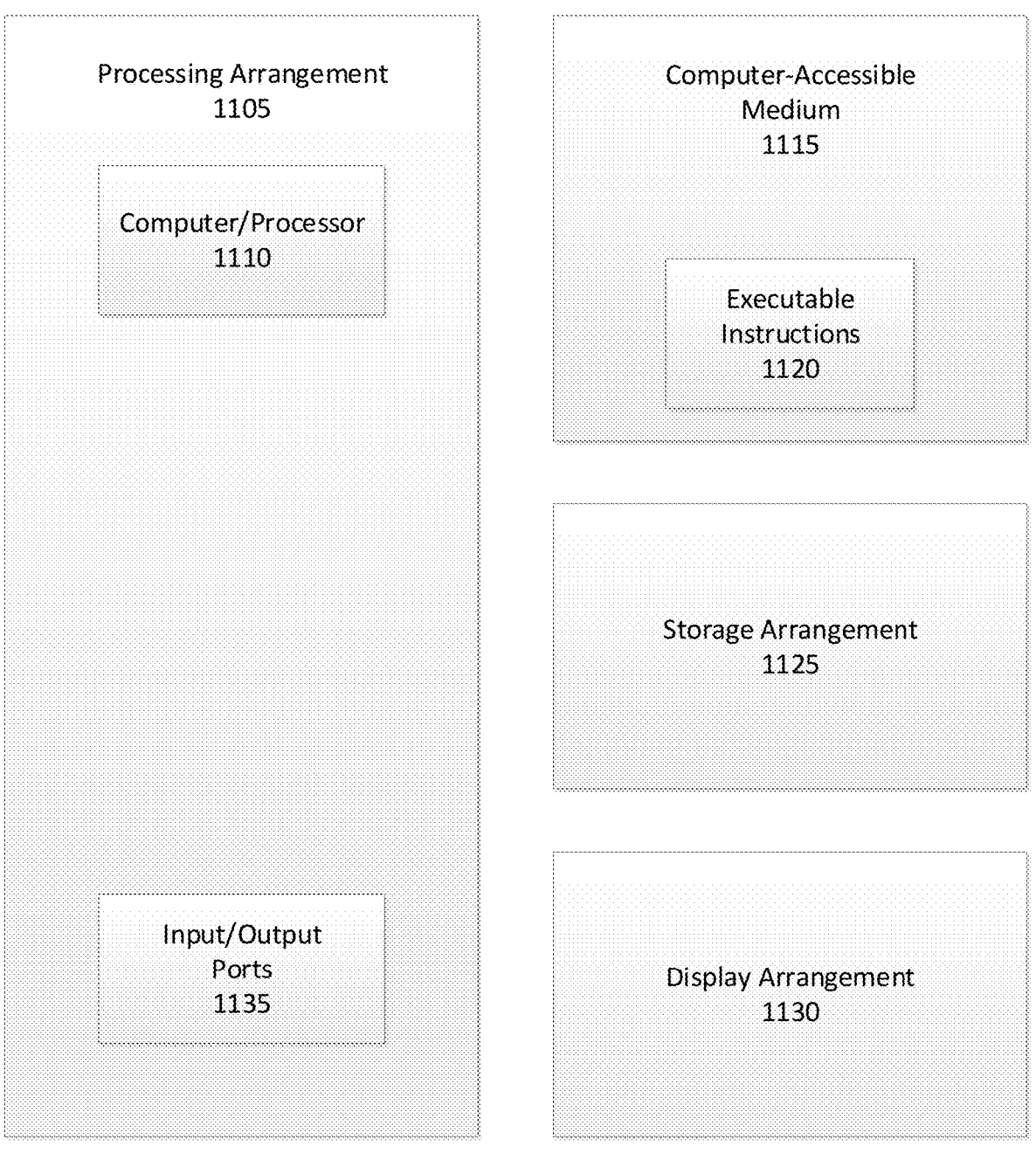
FIG. 11 is an illustration of an exemplary block diagram of an exemplary system in accordance with certain exemplary embodiments of the present disclosure.

FIG. 11 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1105. Such processing/computing arrangement 1105 can be, for example entirely or a part of, or include, but not limited to, a computer/processor 1110 that can include, for example one or more microprocessors, and use instructions stored on a computer-accessible medium (e.g., RAM, ROM, hard drive, or other storage device).

As shown in FIG. 11, for example a computer-accessible medium 1115 (e.g., as described herein above, a storage device such as a hard disk, floppy disk, memory stick, CD-ROM, RAM, ROM, etc., or a collection thereof) can be provided (e.g., in communication with the processing arrangement 1105). The computer-accessible medium 1115 can contain executable instructions 1120 thereon. In addition or alternatively, a storage arrangement 1125 can be provided separately from the computer-accessible medium 1115, which can provide the instructions to the processing arrangement 1105 so as to configure the processing arrangement to execute certain exemplary procedures, processes, and methods, as described herein above, for example.

Further, the exemplary processing arrangement 1105 can be provided with or include an input/output ports 1135, which can include, for example a wired network, a wireless network, the internet, an intranet, a data collection probe, a sensor, etc. As shown in FIG. 11, the exemplary processing arrangement 1105 can be in communication with an exemplary display arrangement 1130, which, according to certain exemplary embodiments of the present disclosure, can be a touch-screen configured for inputting information to the processing arrangement in addition to outputting information from the processing arrangement, for example. Further, the exemplary display arrangement 1130 and/or a storage arrangement 1125 can be used to display and/or store data in a user-accessible format and/or user-readable format.

Exemplary Experimental Validation

ScFvs can be cloned into AND-gate and NOT-gate plasmids. The user can choose the CAR domain into which the scFv will be cloned. T cells can be transduced and transduction efficiency can be assessed. CAR T cells can be co-cultured in vitro with double or single positive target cells to assess their cytotoxicity and the presence on-target, off-tumor (OTOT) toxicity. Patients-derived or cell line tumors (double and/or single positive) can be grafted in nude mice and CAR T cells can be administered to assess their killing ability and OTOT in vivo.

Exemplary Results

Importantly, in almost all cancer types, the current target space has been optimized. However, in HPV-negative head and neck squamous cell carcinoma (HNSC), for which there is currently a dearth of existing CAR targets, there are five new targets that have both superior selectivity and safety scores. Among the HNSC new targets, there are a few that are strongly essentiality in HNSC cell lines.

Further exemplary systems, methods and computer-accessible medium according to the exemplary embodiments of the present disclosure can discover promising target pairs for Uterine corpus endometrial carcinoma (MUC16+EPCAM & MUC16+TACSTD2), Ovarian Cancer (MUC16+ EPCAM), and Breast Cancer (PRLR+EPCAM & PRLR+ TACSTD2). The exemplary systems, methods and computer-accessible medium according to the exemplary embodiments of the present disclosure can determine the target pair of MUC16+EPCAM to be an effective target for Uterine corpus endometrial carcinoma and Breast Cancer indicating it may have determined a target pair that could lead to a CAR construct that could be effective in multiple types of cancer. Exemplary systems, methods and computer-accessible medium according to the exemplary embodiments of the present disclosure can provide the capability to determine and/or identify pan-cancer target pairs.

Figures 16A, 16B, 16C:
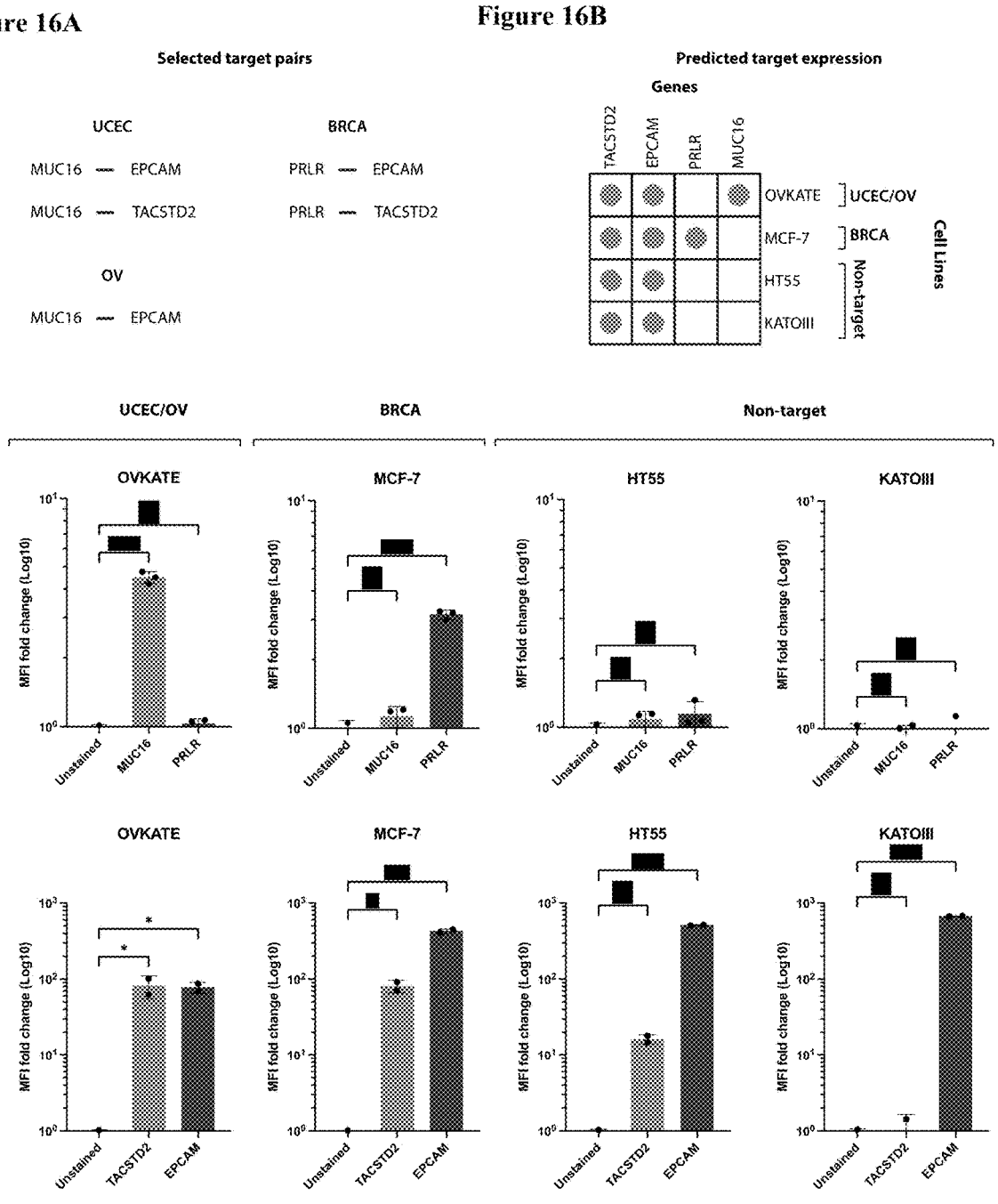
FIG. 16 is a series of exemplary graphs confirming the presence of target pairs identified by exemplary embodiments of the present disclosure in cancer cells lines.

FIG. 16A shows an illustration of target pairs outputted and/or provided by the exemplary systems, methods and computer-accessible medium according to the exemplary embodiments of the present disclosure, specific for Uterine Corpus Endometrial Carcinoma (UCEC), Ovarian Cancer (OV) and Breast Cancer (BRCA). These target pairs were selected to be validated in vitro. FIG. 16B shows an illustration of an exemplary DepMap-predicted expression of the selected genes in target (OVKATE and MCF-7) and non-target (HT55 and KATOIII) cells. The grey dot indicates the expression of the gene in a specific cell line. FIG. 16C shows exemplary graphs providing the Median Fluorescence Intensity (MFI) of selected genes in target (OVKATE and MCF-7) and non-target (HT55 and KATOIII) cells. While EPCAM and TACSTD2 are present in almost all cell lines, PRLR is specifically expressed only in BRCA-derived MCF-7 cell line, while MUC16 is uniquely expressed in OV-derived OVKATE cell line. MFI values were normalized on the unstained control. The p values were calculated using one-way Anova test ($*p<0.05$, $p<0.01$, $*p<0.001$, $****p<0.0001$).

Figure 17:
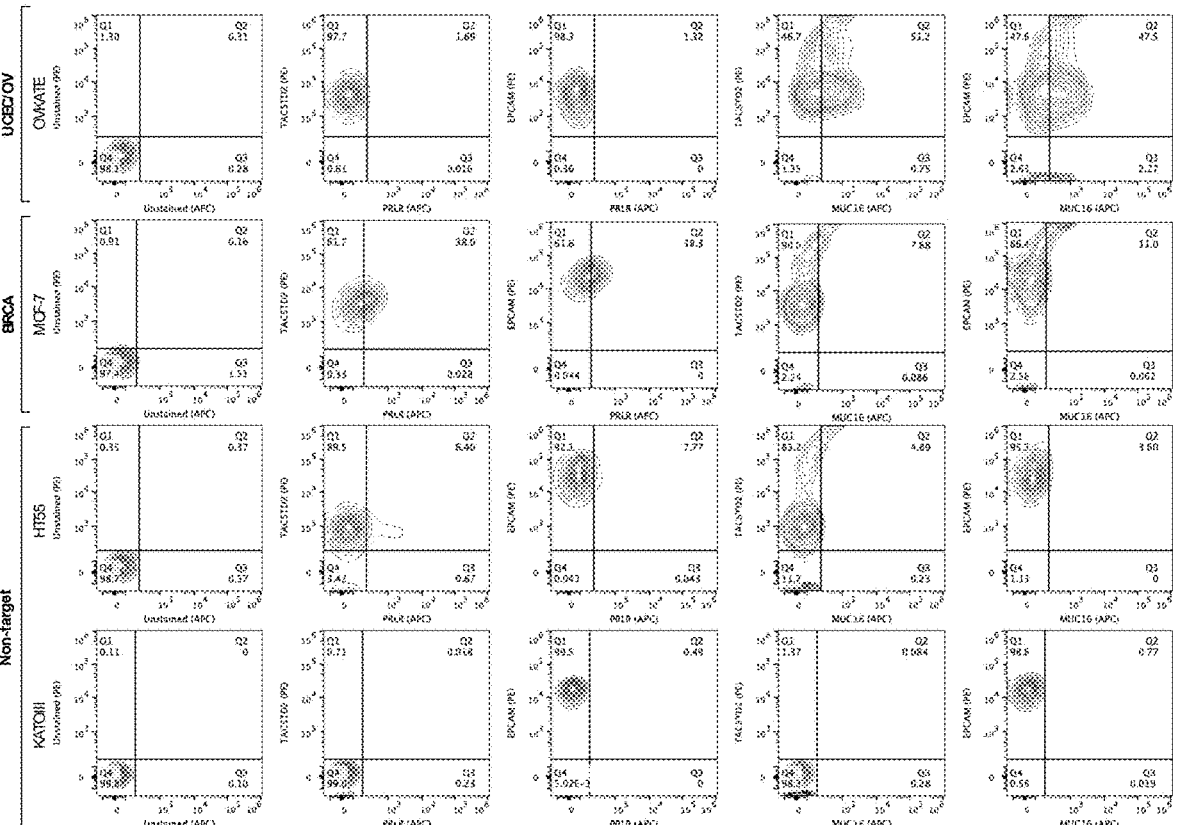
FIG. 17 is exemplary flow cytometry data of MUC16, PRLR, EPCAM and TACSTD2 according to an exemplary embodiment of the present disclosure.

FIG. 17 shows exemplary graphs providing that in vitro validation of exemplary systems, methods and computer-accessible medium according to the exemplary embodiments of the present disclosure confirms the co-expression of target pairs only in target cells and not in non-target cells. Target and non-target cells were stained with antibodies against the membrane proteins MUC16, PRLR, EPCAM and TACSTD2. As determined and/or predicted by the exemplary systems, methods and computer-accessible medium according to the exemplary embodiments of the present disclosure, EPCAM and TACSTD2 are expressed by nearly all cell lines. However, the co-expression of MUC16 with EPCAM (e.g., 47.5%) and TACSTD2 (e.g., 51.2%) may only be observed in the OVKATE cell line, while the co-expression of PRLR with EPCAM (e.g., 38.3%) and TACSTD2 (e.g., 38.0%) can be observed exclusively in MCF-7 cells.

Figure 18:
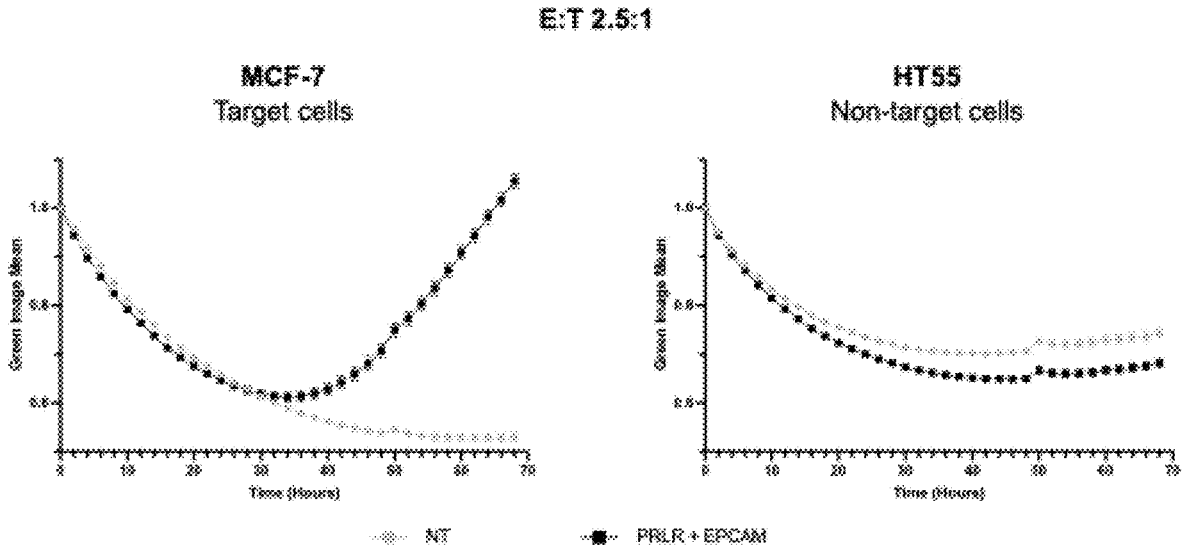
FIG. 18 is a series of in vitro cytotoxic assay confirming that pairs defined by exemplary embodiments of the present disclosure kill target cells without affecting non-target cells.

FIG. 18 shows exemplary graphs providing that in vitro cytotoxic assay confirms that pairs defined by the exemplary systems, methods and computer-accessible medium according to the exemplary embodiments of the present disclosure can kill target cells without affecting non-target cells. SynNotch T cells against software-identified PRLR and EPCAM antigens are able to kills target (MCF-7) but not non-target cells (HT55) when cultured at E:T 2.5:1. In contrast, non-transduced (NT) T cells can exhibit no cytotoxic activity against either target or non-target cells, demonstrating that exemplary systems, methods and computer-accessible medium according to the exemplary embodiments of the present disclosure can effectively determine and/or identify target pairs suitable for use in AND-gated T cell logic systems. The efficiency of cell killing is indicated by a progressive increase in green fluorescence (Green Image Mean) over time.

FIG. 19 shows an exemplary table providing the top generated and/or predicted target pairs by the exemplary systems, methods and computer-accessible medium according to the exemplary embodiments of the present disclosure in Ovarian cancer, Colon adenocarcinoma, Head and neck squamous cell carcinoma, Pancreatic ductal adenocarcinoma, Breast cancer, and Uterine corpus endometrial carcinoma. The suitability scores indicate the quality of a target pair predicted by exemplary systems, methods and computer-accessible medium according to the exemplary embodiments of the present disclosure (a lower suitability scores indicates a better target pair). The last column provides the corresponding target pairs' gene names.

According to the exemplary embodiments of the present disclosure, numerous specific details have been set forth. It is to be understood, however, that implementations of the disclosed technology can be practiced without these specific details. In other instances, well-known methods, structures and techniques have not been shown in detail in order not to obscure an understanding of this description. References to "some examples," "other examples," "one example," "an example," "various examples," "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrases "in one example," "in one exemplary embodiment," or "in one implementation" does not necessarily refer to the same example, exemplary embodiment, or implementation, although it may.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification and drawings, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

Throughout the disclosure, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

This written description uses examples to disclose certain implementations of the disclosed technology, including the best mode, and also to enable any person skilled in the art to practice certain implementations of the disclosed technology, including making and using any devices or systems and performing any incorporated methods.

What is claimed is:

1. A method for providing a cell therapy which includes Chimeric Antigen Receptor (CAR)-T therapy, the method comprising:
   selecting a first set of targets expressed at a first level in cancer and a second level in normal tissues, wherein the first level is higher than the second level;
   selecting a second set of targets that are co-expressed at a third level in cancer and at a fourth level in normal tissues, wherein the third level is higher than the fourth level;
   generating an input set by combining the first and second sets of targets with dependency data, single-cell heterogeneity information and, and antibody availability information;
   determining, with a learning model, at least one target pair for use in CAR-T therapy by identifying at least one gated pair;
   selecting scFv to clone against the determined target pair;
   selecting a configuration for the scFV, wherein the configuration is at least one of Variable Light (VL)-Variable Heavy (VH) or VH-VL
   predicting a value of the determined at least one target pair based on the selected configuration; and
   applying the cell therapy based on the determined at least one target pair,
   wherein the predicted value of the determined at least on target pair is based on one or more of a predicted efficacy information and a predicted safety data.

2. The method of claim 1, wherein the at least one target pair is determined based on a specific type of cancer.

3. The method of claim 1, further comprising ranking the predicted values of each of the at least one target pair.

4. The method of claim 1, wherein the cell therapy is directed toward a solid tumor.

5. The method of claim 1, wherein the at least one target pair is determined to distinguish healthy tissue from cancer.

6. The method of claim 1, wherein the at least one target pair is determined to activate an AND-gated CAR-T cell.

7. The method of claim 1, wherein the at least one target pair is determined to activate a NOT-gated CAR-T cell.

8. A system for Chimeric Antigen Receptor (CAR)-T therapy, comprising:
   at least one processor configured to:
      select a first set of targets expressed at a first level in cancer and a second level in normal tissues, wherein the first level is higher than the second level,
      select a second set of targets that are co-expressed at a third level in cancer and at a fourth level in normal tissues, wherein the third level is higher than the fourth level,
      generate an input set by combining the first and second sets of targets with dependency data, single-cell heterogeneity information and, and antibody availability information, determine, with a learning model, at least one target pair for use in CAR-T therapy by identifying at least one gated pair, select scFv to clone against the determined target pair, select a configuration for the scFV, wherein the configuration is at least one of Variable Light (VL)-Variable Heavy (VH) or VH-VL, predict a value of the determined at least one target pair based on the selected configuration; and direct an application of a cell therapy based on the determined at least one target pair, wherein the predicted value of the determined at least on target pair is based on one or more of a predicted efficacy information and a predicted safety data.

9. The system of claim 8, wherein the at least one target pair is determined based on a specific type of cancer.

10. The system of claim 8, wherein the at least one processor further configured to generate a rank of the predicted values of each of the at least one target pair.

11. The system of claim 8, wherein the cell therapy is directed toward a solid tumor.

12. The system of claim 8, wherein the at least one target pair is determined to distinguish healthy tissue from cancer.

13. The system of claim 8, wherein the at least one target pair is determined to activate an AND-gated CAR-T cell.

14. The system of claim 8, wherein the at least one target pair is determined to activate a NOT-gated CAR-T cell.

15. A non-transitory computer accessible medium which includes software thereon for facilitating Chimeric Antigen Receptor (CAR)-T therapy wherein, when at least one computer processor executes the software, the computer processor is configured to perform the procedures, comprising:

selecting a first set of targets expressed at a first level in cancer and a second level in normal tissues, wherein the first level is higher than the second level;

selecting a second set of targets that are co-expressed at a third level in cancer and at a fourth level in normal tissues, wherein the third level is higher than the fourth level, generating an input set by combining the first and second sets of targets with dependency data, single-cell heterogeneity information and, and antibody availability information, determining, with a learning model, at least one target pair for use in CAR-T therapy by identifying at least one gated pair;

selecting scFv to clone against the determined target pair;

selecting a configuration for the scFV, wherein the configuration is at least one of Variable Light (VL)-Variable Heavy (VH) or VH-VL;

predicting a value of the determined at least one target pair based on the selected configuration; and directing an application of a cell therapy based on the determined at least one target pair, wherein the predicted value of the determined at least on target pair is based on one or more of a predicted efficacy information and a predicted safety data.

16. The non-transitory computer accessible medium of claim 15, wherein the at least one target pair is determined based on a specific type of cancer.

17. The non-transitory computer accessible medium of claim 15, wherein the computer processor is further configured to rank the predicted values of each of the at least one target pair.

18. The non-transitory computer accessible medium of claim 15, wherein the cell therapy is directed toward a solid tumor.

19. The non-transitory computer accessible medium of claim 15, wherein the at least one target pair is determined to distinguish healthy tissue from cancer.

20. The non-transitory computer accessible medium of claim 15, wherein the at least one target pair is determined to activate an AND-gated CAR-T cell.

21. The non-transitory computer accessible medium of claim 15, wherein the at least one target pair is determined to activate a NOT-gated CAR-T cell.

22. A method for automatically generating a Chimeric Antigen Receptor (CAR) sequence, comprising:

identifying a target by determining, with a learning model, at least one target pair for use in CAR-T therapy;

selecting scFv to clone against the identified target;

selecting a configuration for the scFV, wherein the configuration is at least one of Variable Light (VL)-Variable Heavy (VH) or VH-VL;

selecting at least one CAR domain;

predicting a value of the determined at least one target pair based on the selected configuration; and generating the identified target based on the scFv, the configuration, and the at least one CAR domain, wherein the predicted value of the determined at least on target pair is based on one or more of a predicted efficacy information and a predicted safety data.

23. A system for automatically generating a Chimeric Antigen Receptor (CAR) sequence, comprising:

at least one processor configured to;

identify a target by determining, with a learning model, at least one target pair for use in CAR-T therapy, select a scFv to clone against the identified target, select a configuration for the scFV, wherein the configuration is at least one of Variable Light (VL)-Variable Heavy (VH) or VH-VL, select at least one CAR domain, predict a value of the determined at least one target pair based on the selected configuration, and generate the identified target based on the scFv, the configuration, and the at least one CAR domain, wherein the predicted value of the determined at least on target pair is based on one or more of a predicted efficacy information and a predicted safety data.

24. A non-transitory computer accessible medium which includes software thereon for facilitating Chimeric Antigen Receptor (CAR)-T therapy wherein, when at least one computer processor executes the software, the computer processor is configured to perform the procedures, comprising:

identifying a target by determining, with a learning model, at least one target pair for use in CAR-T therapy;

selecting a scFv to clone against the identified target;

selecting a configuration for the scFVs wherein the configuration is at least one of Variable Light (VL)-Variable Heavy (VH) or VH-VL;

selecting at least one CAR domain;

predicting a value of the determined at least one target pair based on the selected configuration; and generating the identified target based on the scFv, the configuration, and the at least one CAR domain, wherein the predicted value of the determined at least on target pair is based on one or more of a predicted efficacy information and a predicted safety data.

* * * * *